United States Patent [19]

Builder et al.

[11] Patent Number: 5,756,672
[45] Date of Patent: May 26, 1998

[54] REFOLDING OF POLYPEPTIDES

[75] Inventors: Stuart Builder, Belmont; Roger Hart, Burlingame; Philip Lester, San Lorenzo; David Reifsnyder, San Mateo, all of Calif.

[73] Assignee: Genentech, Inc., So. San Francisco, Calif.

[21] Appl. No.: 470,108

[22] Filed: Jun. 6, 1995

Related U.S. Application Data

[63] Continuation of Ser. No. 110,664, Aug. 20, 1993.
[51] Int. Cl.$^6$ .................. C07K 14/475; A61K 38/22
[52] U.S. Cl. .............. 530/350; 530/418; 530/419; 530/420; 530/422; 530/423; 530/424; 435/69.1; 435/172.3; 435/320.1; 435/252.3
[58] Field of Search ................... 435/69.4, 69.1, 435/260.2, 172.1, 172.3, 320.1, 252.3, 325; 530/350, 399, 303, 418–420, 421–422, 424, 423

[56] References Cited

U.S. PATENT DOCUMENTS

| | | |
|---|---|---|
| 4,511,502 | 4/1985 | Builder et al. |
| 4,511,503 | 4/1985 | Olson et al. |
| 4,512,922 | 4/1985 | Jones et al. |
| 4,518,256 | 5/1985 | Schwartz. |
| 4,518,526 | 5/1985 | Olson. |
| 4,565,785 | 1/1986 | Gilbert. |
| 4,572,798 | 2/1986 | Koths et al. |
| 4,620,948 | 11/1986 | Builder et al. |
| 4,652,630 | 3/1987 | Bentle et al. |
| 4,673,641 | 6/1987 | George et al. |
| 4,705,848 | 11/1987 | Yang et al. |
| 4,710,473 | 12/1987 | Morris. |
| 4,738,921 | 4/1988 | Bellagaje et al. |
| 4,795,706 | 1/1989 | Hsiung et al. |
| 4,923,967 | 5/1990 | Bobbitt et al. |
| 4,985,544 | 1/1991 | Yokoo et al. |
| 5,019,500 | 5/1991 | Ueda et al. |
| 5,028,531 | 7/1991 | Ueda et al. |
| 5,158,875 | 10/1992 | Miller et al. |
| 5,191,063 | 3/1993 | Inouye et al. |
| 5,288,931 | 2/1994 | Chang et al. |

FOREIGN PATENT DOCUMENTS

| | | |
|---|---|---|
| 128733 | 12/1984 | European Pat. Off. |
| 130166 | 1/1985 | European Pat. Off. |
| 135094 | 3/1985 | European Pat. Off. |
| 196056 | 10/1986 | European Pat. Off. |
| 219814 | 4/1987 | European Pat. Off. |
| 264074 | 4/1988 | European Pat. Off. |
| 286345 | 10/1988 | European Pat. Off. |
| 288451 | 10/1988 | European Pat. Off. |
| 293793 | 12/1988 | European Pat. Off. |
| 302469 | 2/1989 | European Pat. Off. |
| 312358 | 4/1989 | European Pat. Off. |
| 360937 | 4/1990 | European Pat. Off. |
| 361830 | 4/1990 | European Pat. Off. |
| 413440 | 2/1991 | European Pat. Off. |
| 433225 | 6/1991 | European Pat. Off. |
| 62-190199 | 8/1987 | Japan. |
| 63-294796 | 12/1988 | Japan. |
| WO 86/05809 | 10/1986 | WIPO. |
| WO 88/08003 | 10/1988 | WIPO. |
| WO 88/08849 | 11/1988 | WIPO. |
| WO 91/00344 | 1/1991 | WIPO. |
| WO 91/02089 | 2/1991 | WIPO. |
| WO 92/03477 | 3/1992 | WIPO. |
| WO 93/11240 | 6/1993 | WIPO. |
| WO 93/19084 | 9/1993 | WIPO. |

OTHER PUBLICATIONS

Blundell et al., "Tertiary structures, receptor binding, and antigenicity of insulinlike growth factors" *Federation Proc.* 42:2592–2597 (1983).

Boss et al., "Assembly of functional antibodies from immnoglobulin heavy and light chains synthesised in *E. coli*" *Nucleic Acids Research* 12(9): 3791–3806 (1984).

Bowden et al., "Structure and Morphology of Protein Inclusion Bodies in *Escherichia coli*" *Bio/Technology* 9:725–730 (Aug. 1991).

Brems D. et al., "Equilibrium denaturation of pituitary–and recombinant–derived bovine growth hormone" *Biochemistry* 24(26):7662–7668 (1985).

Brems et al., "Altering the association properties of insulin by amino acid replacement" *Protein Engineering* 5(6):527–533 (1992).

Brems et al., "Equilibrium Denaturation of Insulin and Proinsulin" *Biochemistry* 29:9289–9293 (1990).

Brems et al., "Improved insulin stability through amino acid substitution" *Protein Engineering* 5(6):519–525 (1992).

Bryant et al., "Detection of an Equilibrium Intermediate in the Folding of a Monomeric Insulin Analog" *Biochemistry* 31(25): 5692–5698 (1992).

Cabilly et al., "Generation of antibody activity from immunoglobulin polypeptide chains produced in *Escherichia coli*" *Proc. Natl. Acad. Sci. USA* 81:3273–3277 (1984).

Cleland, "Impact of protein folding on biotechnology" *Protein Folding: In Vivo and In Vitro* (ACS Symposium Series 526), Cleland (ed.), Washington, D.C.: American Chemical Society p. 6 (1993).

Cleland et al., "Refolding and Aggregation of Bovine Carbonic Anhydrase B: Quasi–Elastic Light Scattering Analysis" *Biochemistry* 29:11072–11078 (1990).

(List continued on next page.)

*Primary Examiner*—John Ulm
*Assistant Examiner*—Prema Mertz
*Attorney, Agent, or Firm*—Janet E. Hasak

[57] ABSTRACT

A composition is provided comprising about 0.1 to 15 mg/mL of a polypeptide in a buffer having a pH of about 7–12 comprising about 5–40% (v/v) of an alcoholic or polar aprotic solvent, about 0.2 to 3M of an alkaline earth, alkali metal, or ammonium salt, about 0.1 to 9M of a chaotropic agent, and about 0.01 to 15 μM of a copper or manganese salt. The buffer is suitably used in a method for refolding improperly folded polypeptides.

27 Claims, 12 Drawing Sheets

OTHER PUBLICATIONS

Cooke et al., "Solution Structure of Human Insulin–Like Growth Factor 1: A Nuclear Magnetic Resonance and Restrained Molecular Dynamics Study" *Biochemistry* 30:5484–5491 (1991).

Creighton, "Disulfide Bond Formation in Proteins" *Methods in Enzymology* 107:305–329 (1984).

Creighton, "Role of the Environment in the Refolding of Reduced Pancreatic Trypsin Inhibitor" *J. Mol. Biol.* 144:521–550 (1980).

Frank et al., "The Production of Human Proinsulin and its Transformation to Human Insulin and C–Peptide" *Peptides: Synthesis, Structure, Function*, Rich and Gross pp. 729–738 (1981).

Fu and Freire, "On the origin of the enthalpy and entropy convergence temperatures in protein folding" *Proc. Natl. Acad. Sci. USA* 89:9335–9338 (1992).

Funakoshi et al., "Isolation of a Tumor–Derived 186–Residue Peptide Amide Related to Human Chromogranin A and its in vitro Conversion to Human Pancreastatin–48" *Recent Bioactive Peptides and Biology* pp. 512–514 (1989).

Furman et al., "Recombinant Human Insulin–Like Growth Factor II Expressed in *Escherichia coli*" *Bio/Technology* 5:1047–1051 (1987).

George et al., "High–Level Expression in *Escherichia coli* of Biologically Active Bovine Growth Hormone" *DNA* 4:273–281 (1985).

Gill et al., "Recombinant Chicken and Bovine Growth Hormones Accelerate Growth in Aquacultured Juvenile Pacific Salmon *Oncorhynchus kisutch*" *Bio/Technology* 3:643–646 (1985).

Gold, "Purification of Biosynthetic Human Relaxin A–Chain and B–Chain and Scaleup of the Chain Combination Reaction" *Protein Folding and Recovery Symposium* (1992).

Green et al., "Cheddar cheesemaking with recombinant calf chymosin synthesized in *Escherichia coli*" *J. Dairy Research* 52:281–286 (1985).

Halenbeck et al., "Renaturation and Purification of Biologically Active Recombinant Human Macrophage Colony–Stimulating Factor Expressed in *E. coli*" *Bio/Technology* 7:710–715 (1989).

Hejnaes et al., "Development of an optimized refolding process for recombinant Ala–Glu–IGF–1" *Protein Engineering* 5(8): 797–806 (1992).

Hermann, R., "Standard Techniques for Refolding" *Protein Folding* (Chapter 2), 1st edition, Netherlands:European Patent Office p. 1 (1993).

Hober et al., "Disulfide Exchange Folding of Insulin–Like Growth Factor I" *Biochemistry* 31:1749–1756 (1992).

Hoppe et al., "Preparation of Biologically Active Platelet–Derived Growth Factor Type BB from a Fusion Protein Expressed in *Escherichia coli*" *Biochemistry* 28:2956–2960 (1989).

Hua et al., "Two–dimensional NMR studies of Des–(B26–B30)–insulin: sequence–specific resonance assignments and effects of solvent composition" *Biochimica et Biophysica Acta* 1078:101–110 (1991).

Iwai et al., "Direct Identification of Disulfide Bond Linkages in Human Insulin–Like Growth Factor I (IGF–I) by Chemical Synthesis" *J. Biochem.* 106:949–951 (1989).

Jackson et al., "Halogenated alcohols as solvents for proteins: FTIR spectroscopic studies" *Biochimica et Biophysica Acta* 1118:139–143 (1992).

Kohnert et al., "Production of a Recombinant Human Tissue Plasminogen Activator Variant (BM 06.022) from *Escherichia coli* Using a Novel Renaturation Technology" *Fibrinolysis* 4(Suppl. 3, Abs. 116):44 (1990).

Lustig et al., "The Thermal Denaturation of Ribonuclease A in Aqueous–Methanol Solvents" *Biochimica et Biophysica Acta* 1119:205–210 (1992).

Marston, "The purification of eukaryotic polypeptides synthesized in *Escherichia coli*" *Biochemical Journal* 240:1–12 (1986).

Marston et al., "Purification of Calf Prochymosin (Prorennin) Synthesized in *Escherichia coli*" *Bio/Technology* 2:800–804 (Sep. 1984).

Marston et al., "Solubilization of Protein Aggregates" *Meth. Enzymol.* 182(1):264–276 (1990).

Meng et al., "Reduction Studies on Bacterial Recombinant Somatomedin C/Insulin–like Growth Factor–1" *J. Chromaotgraphy* 443:183–192 (1988).

Mitraki et al., "Protein Folding Intermediates and Inclusion Body Formation" *Bio/Technology* 7:690–697 (1989).

Mizukami et al., "Production of Active Human Interferon–β in *E. coli*, I. Preferential Production by Lower Culture Temperature" *Biotechnology Letters* 8(9):605–610 (1986).

Morris et al., "Protein folding/refolding analysis by mass spectrometry–Scrambling of disulphide bridges in insulin" *Biochemical Journal* 268:803–806 (1990).

Murphy et al., "Common Features of Protein Unfolding and Dissolution of Hydrophobic Compounds" *Science* 247:559–561 (1990).

Niwa et al., "Chemical Synthesis, Cloning, and Expression of Genes for Human Somatomedin C (Insulin–like Growth Factor 1) and $^{59}$Val–Somatomedin C" *Annals New York Academy of Sciences* 469:31–52 (1986).

Obukowicz et al., "Secretion and Export of IGF–1 in *Escherichia coli* strain JM101" *Mol. Gen. Genet.* 215:19–25 (1988).

Pocker and Biswas, "Self–Association of Insulin and the Role of Hydrophobic Bonding: A Thermodynamic Model of Insulin Dimerization" *Biochemistry* 20:4354–4361 (1981).

Raschdorf et al., "Location of disulphide bonds in human insulin like growth factors (IGFs) synthesized by recombinant DNA technology" *Biomedical and Environmental Mass Spectrometry* 16:3–8 (1988).

Rinderknecht, "Production of Recombinant Human Relaxin" *Twelfth International Symposium on HPLC of Proteins, Peptides and Polynucleotides* (Sydney, Australia) (1992).

Rudolph et al., "Reactivation of Microbially Produced Human Tissue–Type Plasminogen Activator" *Senior Advisory Group on Biotechnology. Biotechnology International,* London:Century Press pp. 321–322, 324–325 (1991).

Saito et al., "Driect Expression of a Synthetic Somatomedin C Gene in *Escherichia coli* by Use of a Two–Cistron System" *J. Biochem.* 101:1281–1288 (1987).

Saito et al., "Production and Isolation of Recombinant Somatomedin C" *J. Biochem.* 101:123–134 (1987).

Samuelsson et al., "Facilitated In Vitro Refolding of Human Recombinant Insulin–Like Growth Factor I Using a Solubilizing Fusion Partner" *Bio/Technology* 9:363–366 (1991).

Schein et al., "Formation of Soluble Recombinant Proteins in *Escherichia coli* is Favored by Lower Growth Temperature" *Bio/Technology* 6:291–294 (1988).

Schulz et al., "Increased Expression in *Escherichia coli* of a Synthetic Gene Encoding Human Somatomedin C after Gene Duplication and Fusion" *Journal of Bacteriology* 169:5385–5392 (Dec. 1987).

Sekine et al., "Cloning and expression of cDNA for salmon growth hormone in *Escherichia coli*" *Proc. Natl. Acad. Sci. USA* 82:4306–4310 (1985).

Shibata et al., "Biphasic Effects of Alcohols on the Phase Transition of Poly(L-lysine) between α–Helix and β–Sheet Conformations" *Biochemistry* 31:5728–5733.

Smith et al., "Structure and Activity Dependence of Recombinant Human Insulin–Like Growth Factor II on Disulfide Bond Pairing" *Journal of Biological Chemistry* 264(16):9314–9321 (1989).

Snyder, "Free Energy Relationships for Thiol–Disulfide Interchange Reactions between Charged Molecules in 50% Methanol" *Journal of Biological Chemistry* 259(12):7468–7472 (1984).

Spolar et al., "Hydrophobic effect in protein folding and other noncovalent processes involving proteins" *Proc. Natl. Acad. Sci. USA* 86:8382–8385 (1989).

Toren et al., "Determination of Interchain Crosslinkages in Insulin B–Chain Dimers by Fast Atom Bombardment Mass Spectrometry" *Analytical Biochemistry* 169:287–299 (1988).

Tsuji et al., "Characterization of Disulfide Bonds in Recombinant Proteins: Reduced Human Interleukin 2 in Inclusion Bodies and Its Oxidative Refolding" *Biochemistry* 26:3129–3134 (1987).

Wetzel, "Principles of protein stability. Part 2–enhanced folding and stabilization of proteins by suppression of aggregation in vitro and in vivo" *Protein Engineering: A Practical Approach*, Rees et al., ed., Chapter 8, pp. 191–219 (1992).

Wetzel, "Protein Aggregation in vivo—Bacterial Inclusion Bodies and Mammalian Amyloid" *Stability of Protein Pharmaceuticals, Part B: In Vivo Pathways of Degradation and Strategies for Protein Stabilization*, Ahern et al., New York:Plenum Press, Chapter 2, pp. 43–88 (1992).

Wetzel et al., "Mutations in Human Interferon Gamma Affecting Inclusion Body Formation Identified by a General Immunochemical Screen" *Bio/Technology* 9:731–737 (1991).

Wetzel et al., "Production of Biologically Active $N^\alpha$–Desacetyl Thymosin $\alpha_1$ in *Escherichia coli* Expression of a Chemically Synthesized Gene" *Cellular Responses to Molecular Modulators* pp. 251–270 (1981).

Winkler et al., "Purification and Characterization of Recombinant Urokinase from *Escherichia coli*" *Bio/Technology* 3:990–1000 (1985).

Wong et al., "Expression of secreted insulin–like growth factor-1 in *Escherichia coli*" *Gene* 68:193–203 (1988).

Zettlmeissl et al., "Reconstitution of Lactic Dehydrogenase. Noncovalent Aggregation vs. Reactivation. 1. Physical Properties and Kinetics of Aggregation" *Biochemistry* 18(25):5567–5571 (1979).

Zhong et al., "Environment affects amino acid preference for secondary structure" *Proc. Natl. Acad. Sci. USA* 89:4462–4465 (May 1992).

Collard & Gearing (1994). The Cytokine Facts Book, Academic Press, Harcourt Brace & Company, Publishers, pp. 2–3.

Marston (1986) Biochemical Journal, vol. 240, pp. 1–12.

Creighton (1986) Mths in Enzymology vol. 107, pp. 305–329.

FIG. 2

EcoRI (1149)
5'-GAATTCATGAGATTCCTTCAATTTTACTGCAGTTTATTCGCAGCATCCTCCGCATTAGC

TGCTCCAGTCAACACTACAACAGAAGATGAAACGGCACAAATTCCGGCTGAAGCTGTCATCGGTT

ACTTAGATTTAGAAGGGGATTTCGATGTTGCTGTTTTGCCATTTTCCAACAGCACAAATAACGGG

TTATTGTTTATAAATACTACTATTGCCAGCATTGCTGCTAAAGAAGAAGGGGTATCTTTGGATAA

HaeII             PstI
AAGAGGTCCGGAAACTCTGTGCGGCGCTGAGCGTTGAGCGCTCTGCAGTTCGTATGTGGTGATC

BamHI
GAGGCTTCTACTTCAACAAACCGACTGGGTACGGATCCTCCTCGTCGTGCTCCGCAAACCGGC

ATCGTTGATGAATGCTGTTTCGGTCCTGTGACCTTCGCCGTCTGGAAATGTACTGGCTCCGCT

SalI    EcoRI (1633)
GAAACCGGCTAAGTCTGCATAGTCGACGAATTC-3'

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 485 bases
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
GAATTCATGA  GATTTCCTTC  AATTTTTACT  GCAGTTTTAT  TCGCAGCATC      50

CTCCGCATTA  GCTGCTCCAG  TCAACACTAC  AACAGAAGAT  GAAACGGCAC     100

AAATTCCGGC  TGAAGCTGTC  ATCGGTTACT  TAGATTTAGA  AGGGGATTTC     150

GATGTTGCTG  TTTTGCCATT  TTCCAACAGC  ACAAATAACG  GGTTATTGTT     200

TATAAATACT  ACTATTGCCA  GCATTGCTGC  TAAAGAAGAA  GGGGTATCTT     250

TGGATAAAAG  AGGTCCGGAA  ACTCTGTGCG  GCGCTGAGCT  GGTTGACGCT     300

CTGCAGTTCG  TATGTGGTGA  TCGAGGCTTC  TACTTCAACA  AACCGACTGG     350

GTACGGATCC  TCCTCTCGTC  GTGCTCCGCA  AACCGGCATC  GTTGATGAAT     400
```

```
GCTGTTTTCG GTCCTGTGAC CTTCGCCGTC TGGAAATGTA CTGCGCTCCG          450

CTGAAACCGG CTAAGTCTGC ATAGTCGACG AATTC                          485
```

( 2 ) INFORMATION FOR SEQ ID NO:2:

( i ) SEQUENCE CHARACTERISTICS:
        ( A ) LENGTH: 30 bases
        ( B ) TYPE: nucleic acid
        ( C ) STRANDEDNESS: single
        ( D ) TOPOLOGY: linear ( x i ) SEQUENCE DESCRIPTION: SEQ ID NO:2:

```
CATGGCCGGT CCGGAAACTC TGTGCGGCGC                                30
```

( 2 ) INFORMATION FOR SEQ ID NO:3:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( x i ) SEQUENCE DESCRIPTION: SEQ ID NO:3:

```
CGGCCAGGCC TTTGAGACAC GC                                        22
```

( 2 ) INFORMATION FOR SEQ ID NO:4:

( i ) SEQUENCE CHARACTERISTICS:
        ( A ) LENGTH: 51 bases
        ( B ) TYPE: nucleic acid
        ( C ) STRANDEDNESS: single
        ( D ) TOPOLOGY: linear ( x i ) SEQUENCE DESCRIPTION: SEQ ID NO:4:

```
CATGGCCGGT CCCGAAACTC TGTGCGGTGC TGAACTGGTT GACGCTCTGC          50

A                                                               51
```

( 2 ) INFORMATION FOR SEQ ID NO:5:

( i ) SEQUENCE CHARACTERISTICS:
        ( A ) LENGTH: 43 bases
        ( B ) TYPE: nucleic acid
        ( C ) STRANDEDNESS: single
        ( D ) TOPOLOGY: linear ( x i ) SEQUENCE DESCRIPTION: SEQ ID NO:5:

```
CGGCCAGGGC TTTGAGACAC GCCACGACTT GACCAACTGC GAG                 43
```

( 2 ) INFORMATION FOR SEQ ID NO:6:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( x i ) SEQUENCE DESCRIPTION: SEQ ID NO:6:

```
CATGGCCTCC CCATATTC                                             18
```

( 2 ) INFORMATION FOR SEQ ID NO:7:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear -continued ( x i ) SEQUENCE DESCRIPTION: SEQ ID NO:7:

CGGAGGGGTA TAAGGAGC                                                                                    1 8

( 2 ) INFORMATION FOR SEQ ID NO:8:

( i ) SEQUENCE CHARACTERISTICS:
        ( A ) LENGTH: 67 bases
        ( B ) TYPE: nucleic acid
        ( C ) STRANDEDNESS: single
        ( D ) TOPOLOGY: linear ( x i ) SEQUENCE DESCRIPTION: SEQ ID NO:8:

TCGTCGTGCT CCCCAGACTG GTATTGTTGA CGAATGCTGC TTTCGTTCTT                                                  5 0

GCGACCTGCG TCGTCTG                                                                                     6 7

( 2 ) INFORMATION FOR SEQ ID NO:9:

( i ) SEQUENCE CHARACTERISTICS:
        ( A ) LENGTH: 70 bases
        ( B ) TYPE: nucleic acid
        ( C ) STRANDEDNESS: single
        ( D ) TOPOLOGY: linear ( x i ) SEQUENCE DESCRIPTION: SEQ ID NO:9:

AGAACGCTGG ACGCAGCAGA CCTTTACATA ACGCGAGGGG ACTTTGGGCG                                                  5 0

ATTTAGACGA ATCTTCGAGG                                                                                  7 0

REFOLDING OF POLYPEPTIDES

This is a continuation of co-pending application Ser. No. 08/110,664 filed on Aug. 20, 1993, which application is incorporated herein by reference and to which application priority is claimed under 35 USC § 120.

BACKGROUND OF THE INVENTION

1. Field of the Invention

This invention relates to special buffer solutions and their use for refolding polypeptides.

2. Description of Related Art

For commercial production of many polypeptides and proteins, recombinant DNA techniques have become the method of choice because of the large quantities that can be produced in bacteria and other host cells. Manufacturing recombinant protein involves transfecting or transforming host cells with DNA encoding the desired exogenous protein and growing the cells under conditions favoring expression of the recombinant protein. E. coli and yeast are favored as hosts because they can be made to produce recombinant proteins at high titers.

Numerous U.S. patents on general bacterial expression of recombinant-DNA-encoded proteins exist, including U.S. Pat. No. 4,565,785 on a recombinant DNA molecule comprising a bacterial gene for an extracellular or periplasmic carrier protein and non-bacterial gene; No. 4,673,641 on coproduction of a foreign polypeptide with an aggregate-forming polypeptide; No. 4,738,921 on an expression vector with a trp promoter/operator and trp LE fusion with a polypeptide such as insulin-like growth factor (IGF-I); No. 4,795,706 on expression control sequences to include with a foreign protein; and No. 4,710,473 on specific circular DNA plasmids such as those encoding IGF-I.

Under some conditions, certain heterologous proteins expressed in large quantities from bacterial hosts are precipitated within the cells in dense aggregates, recognized as bright spots visible within the enclosure of the cells under a phase-contrast microscope. These aggregates of precipitated proteins are referred to as "refractile bodies," and constitute a significant portion of the total cell protein. Brems et al., *Biochemistry*, 24: 7662 (1985). On the other hand, the aggregates of protein may not be visible under the phase contrast microscope, and the term "inclusion body" is often used to refer to the aggregates of protein whether visible or not under the phase-contrast microscope.

It has been found that the soluble proportion of high-level expressed protein in *E. coli* has been dramatically increased by lowering the temperature of fermentation to below 30° C. A considerable fraction of various foreign proteins, i.e., human interferon-alpha (IFN-α2), interferon-gamma (IFN-γ), and murine MX protein [Schein and Noteborn, *Bio/Technology*, 6: 291–294 (1988)] and human IFN-β [Mizukami et al., *Biotechnol. Lett.*, 8: 605–610 (1986)], stayed in solution. This procedure represents an alternative to renaturation of proteins recovered from refractile bodies, but requires an expression system that is efficiently induced at temperatures below 30° C. The procedure is therefore not effective for all proteins.

For general review articles on refractile bodies, see Marston, supra; Mitraki and King, *Bio/Technology*, 7: 690 (1989); Marston and Hartley, *Methods in Enzymol.*, 182: 264–276 (1990); Wetzel, "Protein Aggregation In Vivo: Bacterial Inclusion Bodies and Mammalian Amyloid," in *Stability of Protein Pharmaceuticals: In Vivo Pathways of Degradation and Strategies for Protein Stabilization*, Ahern and Manning (eds.) (Plenum Press, 1991); and Wetzel, "Enhanced Folding and Stabilization of Proteins by Suppression of Aggregation In Vitro and In Vivo," in *Protein Engineering—A Practical Approach*, Rees, A. R. et al. (eds.) (IRL Press at Oxford University Press, Oxford, 1991).

Recovery of the protein from these bodies has presented numerous problems, such as how to separate the protein encased within the cell from the cellular material and proteins harboring it, and how to recover the inclusion body protein in biologically active form. The recovered proteins are often predominantly biologically inactive because they are folded into a three-dimensional conformation different from that of active protein. For example, misfolded IGF-I with different disulfide bond pairs than found in native IGF-I has significantly reduced biological activity. Raschdorf et al., *Biomedical and Environmental Mass Spectroscopy*, 16: 3–8 (1988). Misfolding occurs either in the cell during fermentation or during the isolation procedure. Methods for refolding the proteins into the correct, biologically active conformation are essential for obtaining functional proteins.

Another property experienced by proteins during refolding is the tendency to produce disulfide-linked dimers, trimers, and multimers. Morris et al., *Biochem. J.*, 268: 803–806 (1990); Toren et al., *Anal. Biochem.*, 169: 287–299 (1988); Frank et al., in *Peptides: synthesis-structure-function,* ed. D. H. Rich and E. Gross, pp. 729–738 (Pierce Chemical Company: Rockford, Ill., 1981). This association phenomenon is very common during protein refolding, particularly at higher protein concentrations, and appears often to involve association through hydrophobic interaction of partially folded intermediates. Cleland and Wang, *Biochemistry*, 29: 11072–11078 (1990).

Protein folding is influenced by the nature of the medium containing the protein and by a combination of weak attractive or repellent intramolecular forces involved in hydrogen bonding, ionic bonding, and hydrophobic interactions. When pairs of cysteine residues are brought into close proximity as the peptide backbone folds, strong covalent disulfide bonds form between cysteine residues, serving to lock the tertiary conformation in place. Refolding protocols have been designed to break incorrect disulfide bonds, block random disulfide bonding, and allow refolding and correct disulfide bonding under conditions favorable to the formation of active conformer.

One series of techniques for recovering active protein from inclusion bodies involves solubilizing the inclusion bodies in strongly denaturing solutions and then optionally exchanging weakly denaturing solutions for the strongly denaturing solutions (or diluting the strong denaturant), or using molecular sieve or high-speed centrifugation techniques. Such recovery methods, described, e.g., in U.S. Pat. Nos. 4,512,922; 4,518,256; 4,511,502; and 4,511,503, are regarded as being universally applicable, with only minor modifications, to the recovery of biologically active recombinant proteins from inclusion bodies. These methods seek to eliminate random disulfide bonding prior to coaxing the recombinant protein into its biologically active conformation through its other stabilizing forces.

In one method for recovering protein from inclusion bodies, the denatured protein desired to be refolded is further purified under reducing conditions that maintain the cysteine moieties of the protein as free sulfhydryl groups. The reducing agent is then diluted into an aqueous solution to enable the refolded protein to form the appropriate disulfide bonds in the presence of air or some other oxidizing agent.

This enables refolding to be easily incorporated into the overall purification process.

In another approach, refolding of the recombinant protein takes place in the presence of both the reduced (R-SH) and oxidized (R-S-S-R) forms of a sulfhydryl compound. This allows free sulfhydryl groups and disulfides to be formed and reformed constantly throughout the purification process. The reduced and oxidized forms of the sulfhydryl compound are provided in a buffer having sufficient denaturing power that all of the intermediate conformations of the protein remain soluble in the course of the unfolding and refolding. Urea is suggested as a suitable buffer medium because of its apparent ability to act both as a sufficiently weak denaturing agent to allow the protein to approximate its correct conformation and as a sufficiently strong denaturant that the refolding intermediates maintain their solubility.

The third alternative in this series is designed to break any disulfide bonds that may have formed incorrectly during isolation of the inclusion bodies and then to derivatize the available free sulfhydryl groups of the recombinant protein. This objective is achieved by sulfonating the protein to block random disulfide pairings, allowing the protein to refold correctly in weak denaturant, and then desulfonating the protein, under conditions that favor correct disulfide bonding. The desulfonation takes place in the presence of a sulfhydryl compound and a small amount of its corresponding oxidized form to ensure that suitable disulfide bonds will remain intact. The pH is raised to a value such that the sulfhydryl compound is at least partially in ionized form to enhance nucleophilic displacement of the sulfonate.

These refolding protocols, while practical for their universal utility, have not been shown necessarily to be maximally efficient with, for example, recombinant IGF-I.

The recovery of the biological activity requires a carefully monitored renaturation procedure and may be very difficult depending on the protein in question. A number of publications have appeared that report refolding attempts for individual proteins that are produced in bacterial hosts or are otherwise in a denatured or non-native form. For example, formation of a dimeric, biologically active macrophage-colony stimulating factor (M-CSF) after expression in *E. coli* is described in WO 88/8003 and by Halenbeck et al., *Biotechnology*, 7: 710–715 (1989). The procedures described involve the steps of initial solubilization of M-CSF monomers isolated from inclusion bodies under reducing conditions in a chaotropic environment comprising urea or guanidine hydrochloride, refolding achieved by stepwise dilution of the chaotropic agents, and final oxidation of the refolded molecules in the presence of air or a redox-system.

U.S. Pat. No. 4,923,967 and EP 361,830 describe a protocol for solubilizing and sulphitolysing refractile protein in denaturant, then exchanging solvent to precipitate the protein. The protein is resolubilized in denaturant and allowed to refold in the presence of reducing agent. The multiple steps required to achieve correct folding are time-consuming.

Methods for refolding proteins have been reported for several proteins such as interleukin-2 (IL-2) [Tsuji et al., *Biochemistry*, 26: 3129–3134 (1987); WO 88/8849 (which discloses on p. 17 use of high concentrations of copper as oxidant], growth hormone from various sources [George et al., DNA, 4: 273–281 (1984); Gill et al., *Bio/Technology*, 3: 643–646 (1985); Sekine et al., *Proc. Natl. Acad. Sci. USA*, 82: 4306–4310 (1985); U.S. Pat. No. 4,985,544, the lattermost reference involving adding a denaturing agent and reducing agent to solubilize the protein, removing the reducing agent, oxidizing the protein, and removing the denaturing agent], prochymosin [Green et al., *J. Dairy Res.*, 52: 281–286 (1985)], urokinase [Winkler et al., *Bio/Technology*, 3: 990–1000 (1985)], somatotropin [U.S. Pat. No. 4,652,630, whereby urea is used for solubilization, and a mild oxidizing agent is then used for refolding], interferon-beta [EP 360,937 published Apr. 4, 1990], and tissue-plasminogen activator [Rudolph et al., in "623rd Biochem. Soc. Meeting," Canterbury (1987)]. See also Marston, *Biochemical J.*, 240: 1–12 (1986). An additional folding procedure using the pro-sequence of the naturally occurring polypeptide to promote folding of a biologically inactive polypeptide to its active form, exemplified by subtilisin, is disclosed in U.S. Pat. No. 5,191,063.

In certain recovery techniques, up to at least 60% active foreign protein has been obtained. See, e.g., Boss et al., *Nucl. Acids Res.*, 12: 3791–3806 (1984); Cabilly et al., *Proc. Natl. Acad. Sci. USA*, 81: 3273–3277 (1984); Marston et al., *Bio/Technology*, 2: 800–804 (1984); Rudolph et al., supra.

Additional representative literature on refolding of non-native proteins derived from different sources include a report that IL-2 and interferon-β (IFN-β) have been refolded using SDS for solubilization and $Cu^{+2}$ ions as oxidation promoters of the fully reduced proteins. U.S. Pat. No. 4,572,798. A process for isolating recombinant refractile proteins as described in U.S. Pat. No. 4,620,948 involves using strong denaturing agents to solubilize the proteins, reducing conditions to facilitate correct folding, and denaturant replacement in the presence of air or other oxidizing agents to reform the disulfide bonds. The proteins to which the process can be applied include urokinase, human, bovine, and porcine growth hormone, interferon, tissue-type plasminogen activator, foot-and-mouth disease (FMD) coat protein, pro-renin, and a src protein.

A method for renaturing unfolded proteins including cytochrome c, ovalbumin, and trypsin inhibitor by reversibly binding the denatured protein to a solid matrix and stepwise renaturing it by diluting the denaturant is disclosed in WO 86/5809. A modified monomeric form of human platelet-derived growth factor (PDGF) expressed in *E. coli* has been S-sulfonated during purification to protect thiol moieties and then dimerized in the presence of oxidizing agents to yield the active protein. Hoppe et al., *Biochemistry*, 28: 2956–2960 (1989).

Additionally, EP 433,225 published Jun. 19, 1991 discloses a process for producing dimeric biologically active transforming growth factor-β protein or a salt thereof wherein the denatured monomeric form of the protein is subjected to refolding conditions that include a solubilizing agent such as mild detergent, an organic, water-miscible solvent, and/or a phospholipid. U.S. Pat. No. 4,705,848 discloses the isolation of monomeric, biologically active growth hormone from inclusion bodies using one denaturing step with a guanidine salt and one renaturing step. See also Bowden et al., *Bio/Technology*, 9: 725–730 (1991) on β-lactamase cytoplasmic and periplasmic inclusion bodies, and Samuelsson et al., *Bio/Technology*, 9: 731 (1991) on refolding of human interferon-gamma mutants. Moreover, Hejnaes et al., *Protein Engineering*, 5: 797–806 (1992) describes use of a chaotropic agent with IGF-I.

Several literature references exist on the production of IGF-I in bacteria. These include EP 128,733 published Dec. 19, 1984 and EP 135,094 published Mar. 27, 1985, which address expression of IGF-I in bacteria. EP 288,451 addresses use of lamB or ompF signal to secrete IGF-I in bacteria; Obukowicz et al., *Mol. Gen. Genet.*, 215: 19–25 (1988) and Wong et al., *Gene*, 68: 193–203 (1988) teach similarly. EP 286,345 discloses fermentation of IGF-I using a lambda promoter.

In addition, methods have been suggested for preparing IGF-I as a fusion protein. For example, EP 130,166 discloses expression of fusion peptides in bacteria, and U.S. Pat. No. 5,019,500 and EP 219,814 disclose a fusion of IGF-I with a protective polypeptide for expression in bacteria. EP 264,074 discloses a two-cistronic met-IGF-I expression vector with a protective peptide of 500–50,000 molecular weight [see also U.S. Pat. No. 5,028,531 and Saito et al., *J. Biochem.*, 101: 1281–1288 (1987)]. Other IGF-I fusion techniques include fusion with protective peptide from which a rop gene is cut off [EP 219,814], IGF-I multimer expression [Schulz et al., *J. Bacteriol.*, 169: 5385–5392 (1987)], fusion of IGF-I with luteinizing hormone (LH) through a chemically cleavable methionyl or tryptophan residue at the linking site [Saito et al., *J. Biochem.*, 101: 123–134 (1987)], and fusion with superoxide dismutase. EP 196,056. Niwa et al., *Ann. NY Acad. Sci.*, 469: 31–52 (1986) discusses the chemical synthesis, cloning, and successful expression of genes for IGF-I fused to another polypeptide. These methods utilizing fusion proteins, however, generally require a relatively long leader sequence and are directed to improving expression of the inclusion body protein, not to improving refolding of the denatured recombinant protein.

U.S. Pat. No. 5,158,875 describes a method for refolding recombinant IGF-I that involves cloning the IGF-I gene with a positively charged leader sequence prior to transfecting the DNA into the host cell. The additional positive charge on the amino terminus of the recombinant IGF-I promotes correct refolding when the solubilized protein is stirred for 2–16 hours in denaturant solution. Following refolding, the leader sequence is cleaved and the active recombinant protein is purified. However, this multistep process is burdensome, requiring additional materials and effort to clone a heterologous leader sequence in front of the IGF-I gene and then to remove the leader sequence from the purified protein.

Another method for facilitating in vitro refolding of recombinant IGF-I involves using a solubilized affinity fusion partner consisting of two IgG-binding domains (ZZ) derived from staphylococcal protein A. See Samuelsson et al., supra. This method uses the protein A domain as a solubilizer of misfolded and multimeric IGF-I. While this method does not use denaturing agents or redox chemicals, it involves the extra steps of fusing onto the IGF-I gene a separate gene and removing the polypeptide encoded by that gene after expression of the fusion gene.

Other investigators have described studies of IGF-I refolding involving disulfide exchange equilibration of refolding intermediates. For example, the refolding of IGF-I using redox buffers was investigated and the partially oxidized IGF-I forms produced were characterized by Hober et al., *Biochemistry*, 31: 1749–1756 (1992).

Disulfide exchange can also be modulated using the additive agent of peptidyl disulfide isomerase (PDI) or peptidyl prolyl isomerase (PPI). See, for example, JP Pat. Appln. No. 63294796 published Dec. 1, 1988; EP 413,440 published Feb. 20, 1991; and EP 293,793 published Dec. 7, 1988.

Enhancement of selected disulfide pairings by adding 50% methanol to buffer at low ionic strength has been reported by Snyder, *J. Biol. Chem.*, 259: 7468–7472 (1984). The strategy involves enhancing formation of specific disulfide bonds by adjusting electrostatic factors in the medium to favor the juxtaposition of oppositely charged amino acids that border the selected cysteine residues. See also Tamura et al., abstract and poster presented at the Eleventh American Peptide Symposium on Jul. 11, 1989 advocating addition of acetonitrile, DMSO, methanol, or ethanol to improve the production of the correctly folded IGF-I.

A method for folding AlaGlu-IGF-I involving changing the redox potential by dialysis against a buffer containing from 20–40% v/v ethanol over a period of up to five hours and acidifying the mixture is disclosed in WO 92/03477 published Mar. 5, 1992.

Methanol was used at certain concentrations in the denaturation of ribonuclease. Lustig and Fink, *Biochim. Biophys. Acta*, 1119: 205–210 (1992). Studies by other laboratories indicate that moderate concentrations of alcohol can reduce association of insulin-like peptides under conditions that promote structure destabilization. Bryant et al., *Biochemistry*, 31: 5692–5698 (1992); Hua and Weiss, *Biochim. Biophys. Acta*, 1078: 101–110 (1991); Brems et al., *Biochemistry*, 29: 9289–9293 (1990); Ueda et al., JP 62-190199 published Jul. 20, 1987.

Research by other investigators has shown that solution polarity influences the propensity of peptides to acquire certain secondary structure. Jackson and Mantsch, *Biochim Biophys. Acta*, 1118: 139–143 (1992); Shibata et al., *Biochemistry*, 31: 5728–5733 (1992); Zhong and Johnson, *Proc. Natl. Acad. Sci. USA*, 89: 4462–4465 (1992). In general, reduced solution polarity appears to favor formation of alpha helix in short peptides. Jackson and Mantsch, supra. Spectroscopic studies on insulin also indicate that moderate concentrations of alcohols enhance alpha helix content. Hua and Weiss, supra.

There is a need for an efficient and inexpensive procedure for refolding polypeptides, including insoluble, misfolded IGF-I and others, into the correct conformation so that the biological activity of the polypeptide can be restored.

Accordingly, it is an object of the present invention to provide an efficient refolding method for polypeptides.

It is another object to provide a refolding method that does not utilize expensive disulfide-exchange reagents such as glutathione.

It is a further object to provide a refolding method that does not produce a product containing disulfide adducts.

It is a still further object to provide refolding conditions that are maximally repeatable, robust and scalable.

These and other objects will be apparent to those of ordinary skill in the art.

SUMMARY OF THE INVENTION

It has now been found that the use of low copper or manganese concentrations greatly facilitates disulfide oxidation of polypeptides. Accordingly, the present invention provides a composition comprising about 0.1 to 15 mg/mL of a polypeptide in a buffer of pH 7–12 comprising about 5–40% (v/v) of an alcoholic or polar aprotic solvent, about 0.2 to 3M of an alkaline earth, alkali metal, or ammonium salt, about 0.1 to 9M of a chaotropic agent, and about 0.01 to 15 µM of a copper or manganese salt.

In another aspect, this invention provides a process for increasing the yield of correct refolding of a misfolded polypeptide contained in host cells, wherein during the refolding step the polypeptide is present in a concentration of about 0.1 to 15 mg/mL in a buffer of pH 7–12 comprising about 5–40% (v/v) of an alcoholic or polar aprotic solvent, about 0.2 to 3M of an alkaline earth, alkali metal, or ammonium salt, about 0.1 to 9M of a chaotropic agent, and about 0.01 to 15 μM of a copper or manganese salt.

In still another aspect, the invention supplies a process for reactivating misfolded IGF-I contained in host cells, which process comprises:

(a) isolating said IGF-I from the host cells;

(b) maintaining said IGF-I in an alkaline buffer comprising a chaotropic agent and a reducing agent in amounts sufficient for solubilization; and (c) incubating said solubilized IGF-I at a concentration of about 0.1 to 15 mg/mL in a folding buffer of pH 7–12 comprising about 5–40% (v/v) of an alcoholic or polar aprotic solvent, about 0.2 to 3M of an alkaline earth, alkali metal, or ammonium salt, about 0.1 to 9M of a chaotropic agent, and about 0.01 to 15 μM of a copper or manganese salt, wherein an oxygen source is introduced, so that refolding of the IGF-I occurs during the incubation.

The essence of the invention is in utilizing a special buffer containing a minimal concentration of copper or manganese salt to enhance refolding of misfolded polypeptides. The use of manganese or copper salts as oxidation catalysts avoids the necessity of more expensive disulfide-exchange agents such as glutathione. Furthermore, the method avoids the possibility of producing polypeptide containing disulfide adducts that can result when disulfide-exchange agents are employed. In one preferred embodiment, solution conditions are identified that are favorable for refolding misfolded IGF-I recovered from prokaryotic periplasmic refractile bodies to obtain high-yield, properly folded IGF-I.

In particular, the process is preferred for non-native mammalian polypeptides produced recombinantly in prokaryotic cells, such as bacteria, including E. coli, which form refractile bodies in the periplasm of the cells. In addition, the invention herein results in higher yields of protein regardless of the protein concentration employed in the reaction mixture.

BRIEF DESCRIPTION OF THE DRAWINGS

FIG. 2 depicts the nucleotide sequence of the EcoRI—EcoRI fragment (from positions 1149 to 1633) of p200 containing the MF alpha I prepro and IGF-I gene sequences (SEQ. ID NO. 1).

DESCRIPTION OF THE PREFERRED EMBODIMENTS

A. Definitions

Figure 1:
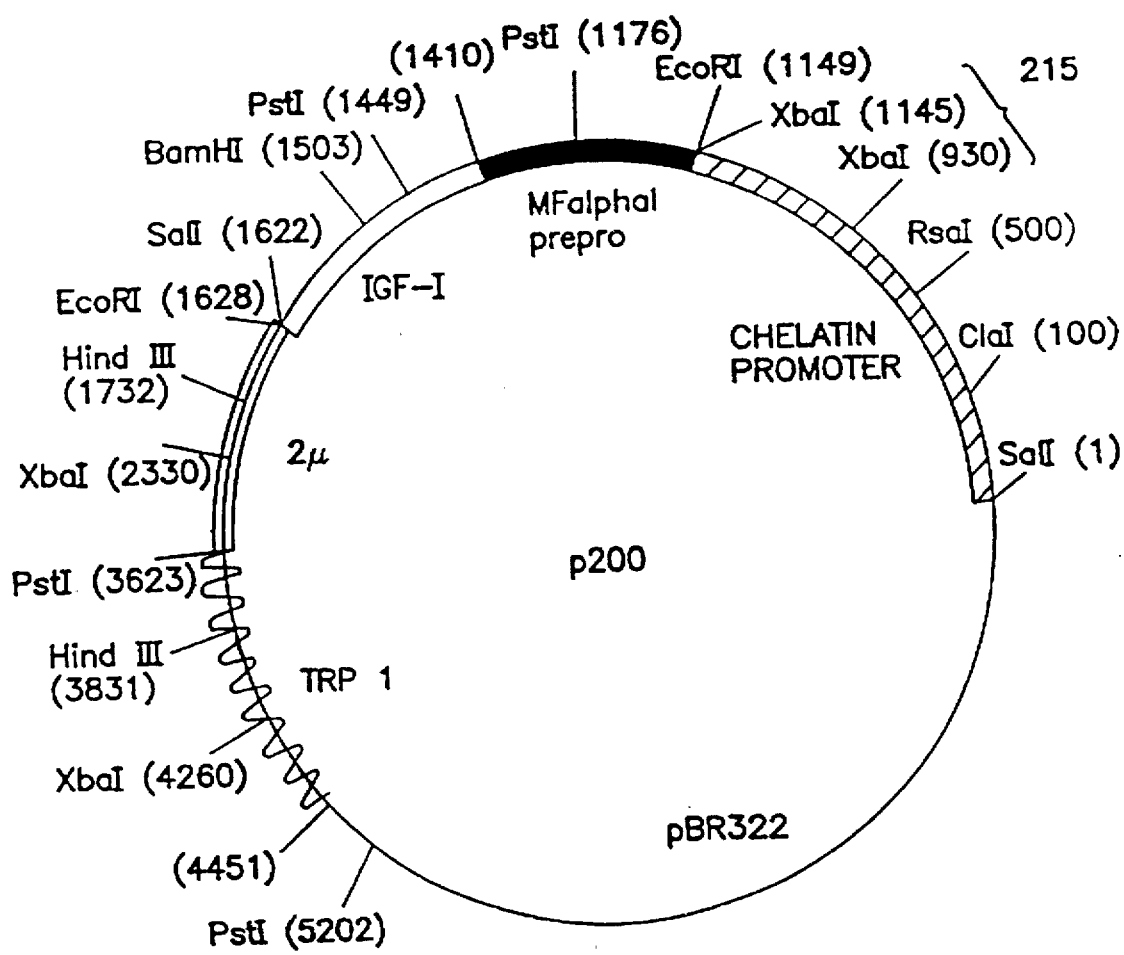
FIG. 1 shows a restriction map for plasmid p200, used to produce pLamBIGF, an intermediate plasmid in the production of pLBIGFTsc, used to prepare pBKIGF-2, an intermediate plasmid in preparing an expression vector encoding IGF-I, namely, pBKIGF-2B.

As used herein, "polypeptide of interest" refers generally to peptides and proteins having more than about ten amino acids. The polypeptides may be homologous to the host cell, or preferably, may be exogenous, meaning that they are heterologous, i.e., foreign, to the host cell being utilized, such as a human protein produced by a Chinese hamster ovary cell or by a bacterial cell, or a yeast polypeptide produced by a different yeast or a bacterial or mammalian cell. Preferably, mammalian polypeptides (polypeptides that were originally derived from a mammalian organism) are used, more preferably those produced in prokaryotic cells, more preferably as inclusion bodies in bacterial cells, especially from the periplasm of the bacteria.

Examples of bacterial polypeptides include, e.g., alkaline phosphatase and β-lactamase. Examples of mammalian polypeptides include molecules such as, e.g., renin, a growth hormone, including human growth hormone; bovine growth hormone; growth hormone releasing factor; parathyroid hormone; thyroid stimulating hormone; lipoproteins; α1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial naturietic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; a serum albumin such as human serum albumin; mullerian-inhibiting substance; relaxin A-chain; relaxin B-chain; prorelaxin; mouse gonadotropin-associated peptide; a microbial protein, such as beta-lactamase; Dnase; inhibin; activin; vascular endothelial growth factor; receptors for hormones or growth factors; integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; antibodies; and fragments of any of the above-listed polypeptides.

The preferred polypeptides of interest are those that are easily produced in prokaryotic cells with a minimum of proteolysis and need not be glycosylated for their intended utility. Examples of such mammalian polypeptides include IGF-I, IGF-II, brain IGF-I, growth hormone, relaxin chains, growth hormone releasing factor, insulin chains or proinsulin, urokinase, immunotoxins, NGF, NT-5, and antigens. Particularly preferred mammalian polypeptides include IGF-I, brain IGF-I, growth hormone, and a neurotrophin such as NGF, NT-3, NT-4, NT-5, and NT-6, including NT-5, and the most preferred mammalian polypeptide is IGF-I.

As used herein, "IGF-I" refers to insulin-like growth factor-I from any species, including bovine, ovine, porcine, equine, and preferably human, in native sequence or in variant form and recombinantly produced. One method for producing IGF-I is described in EP 128,733 published Dec. 19, 1984.

As used herein, the term "in a non-native conformation" describes polypeptides that assume a secondary, tertiary, and/or quaternary structure that is not the native equivalent. The polypeptide may be in such conformation at any point in the claimed process herein, whether before the contacting step or during or after the contact with chaotropic agent and phase-forming species. The polypeptide in this non-native conformation may be soluble but in an inactive form or may be a non-native membrane protein, or may be insoluble and in a biologically inactive conformation with mismatched or unformed disulfide bonds. This insoluble polypeptide is preferably, but need not be, contained in retractile bodies, i.e., it may or may not be visible under a phase contrast microscope.

As used herein, the term "incorrectly folded" polypeptides refers to precipitated or aggregated polypeptides that are contained within refractile bodies. Non-native polypeptides are obtained from incorrectly folded polypeptides and include correctly folded and misfolded material.

The term "inclusion bodies" or "refractile bodies" refers to dense intracellular masses of aggregated polypeptide of interest, which constitute a significant portion of the total cell protein, including all cell components. In some cases, but not all cases, these aggregates of polypeptide may be recognized as bright spots visible within the enclosure of the cells under a phase-contrast microscope at magnifications down to 1000 fold.

As used herein, the term "cells" refers to any cells; the cells from which the polypeptide of interest is recovered can be treated with the phase-forming reagents and refolding reagents no matter what their status. For example, the invention encompasses cells in cell culture (whole broth wherein the cells are not separated irrespective of the tank where they are grown) as well as those which have been subjected to homogenization or centrifugation. The phrase "cell culture" refers not only to mammalian cell cultures, but to cultures of any cells, including prokaryotic and yeast cells.

The term "conformers" refers to polypeptides that differ only in intramolecular disulfide bonding. For example, IGF-I is 70 amino acids long and has six cysteine residues that form intramolecular disulfide bonds. The correct, active IGF-I conformer has disulfide bonds between amino acid residues C6–C48, C47–C52, and C18–C61. The other main polypeptide is a biologically less active conformer having disulfide bonds between amino acid residues C6–C47, C48–C52, and C18–C61.

As used herein, the term "fermentation vessel" refers to a tank or other apparatus wherein the culturing of the prokaryotic host takes place so as to produce the polypeptide of interest. The fermentation broth or medium is the culturing medium used for the cells.

As used herein, "chaotropic agent" refers to a compound that, in a suitable concentration in aqueous solution, is capable of changing the spatial configuration or conformation of polypeptides through alterations at the surface thereof so as to render the polypeptide soluble in the aqueous medium. The alterations may occur by changing, e.g., the state of hydration, the solvent environment, or the solvent-surface interaction. The concentration of chaotropic agent will directly affect its strength and effectiveness. A strongly denaturing chaotropic solution contains a chaotropic agent in large concentrations which, in solution, will effectively unfold a polypeptide present in the solution. The unfolding will be relatively extensive, but reversible. A moderately denaturing chaotropic solution contains a chaotropic agent which, in sufficient concentrations in solution, permits partial folding of a polypeptide from whatever contorted conformation the polypeptide has assumed through intermediates soluble in the solution, into the spatial conformation in which it finds itself when operating in its active form under endogenous or homologous physiological conditions. Examples of chaotropic agents include guanidine hydrochloride, urea, and hydroxides such as sodium or potassium hydroxide. Chaotropic agents include a combination of these reagents, such as a mixture of base with urea or guanidine hydrochloride.

As used herein, "reducing agent" refers to a compound that, in a suitable concentration in aqueous solution, maintains sulfhydryl groups so that the intra- or intermolecular disulfide bonds are chemically disrupted. Representative examples of suitable reducing agents include dithiothreitol (DTT), dithioerythritol (DTE), beta-mercaptoethanol (BME), cysteine, cysteamine, thioglycolate, glutathione, and sodium borohydride.

As used herein, "phase-forming species" or "phase-forming reagents" refers to molecules that will act to form multiple phases when added to an aqueous solution. An "aqueous" solution is one wherein the majority of the solution (i.e., greater than about 50%) constitutes water. Thus, for example, 40% ethanol, which contains about 60% water, is a suitable solvent for a phase-forming species. Examples of phase-forming species include polymer-polymer combinations, solvent-salt combinations, polymer-salt combinations, and polymer-solvent combinations. Most preferred herein is the polymer-salt combination.

As used herein, "biomass solids and nucleic acids" refers to particulate (non-dissolved) solids that result (or originate)

from the cells or cell culture in which the polypeptide is produced, as well as nucleic acids (DNA, RNA). This would include all sources other than solubilization and liquid extraction component addition. Such solids include, for example, cells, cell debris, media components, cell membranes and vesicles, and proteins endogenous to the cell that are not soluble proteins or other insoluble components of the cell. Upon practicing the method of this invention, the biomass solids and nucleic acids are found in an opposite phase from the polypeptide.

As used herein, the term "multiple" as applied to phases means more than one phase, preferably two to four phases, and most preferably two phases. A phase "enriched in the polypeptide and depleted in biomass solids" refers to a phase wherein the polypeptide has a partition coefficient greater than one and the biomass solids have a partition coefficient less than one, where the partition coefficient is referenced to the phase of interest. For example, if the lower phase is enriched in product, then the partition coefficient is the concentration in the bottom phase divided by the concentration in the top phase.

As used herein, "osmolyte" refers to an agent that lends osmolality to the buffered solution or affects hydration or surface tension. Examples include polyols and sugars such as glycerol, erythritol, arabitol, sorbitol, mannitol, xylitol, mannisidomannitol, glycosyl glycerol, glucose, fructose, sucrose, trehalose, and isofluoroside; polymers such as dextrans, levans, and polyethylene glycol; and some amino acids and derivatives thereof such as glycine, alanine, β-alanine, proline, taurine, betaine, octopine, glutamate, sarcosine, y-aminobutyric acid, and trimethylamine N-oxide (TMAO), as described more fully in Yancey et al., *Science*, 217: 1214–1222 (1982) and Schein, *Bio/Technology*, 8: 308–315 (1990).

As used herein, "buffer" refers to a buffered solution that resists changes in pH by the action of its acid-base conjugate components.

As used herein, "solvent" refers to alcohols and polar aprotic solvents. Alcohols are meant in the sense of the commonly used terminology for alcohol, preferably alcohols with 1 to 10 carbon atoms, more preferably methanol, ethanol, iso-propanol, n-propanol, or t-butanol, as well as glycerol, propylene glycol, ethylene glycol, polypropylene glycol, and polyethylene glycol, and most preferably ethanol or iso-propanol. Such alcohols are solvents that, when added to aqueous solution, increase the hydrophobicity of the solution by decreasing solution polarity. Polar aprotic solvents are such molecules as dimethyl sulfoxide (DMSO), dimethyl formamide (DMF), N-methylpyrrolidone (NMP), tetrahydrofuran (THF), dioxane, acetonitrile, etc., that can be used in place of or in addition to the alcohol.

As used herein, the phrase "alkaline earth, alkali metal, or ammonium salt" refers to a salt having a cation from the alkaline earth or alkali metal elements or an ammonium cation and having an inorganic or organic (hydrocarbon-based) anion. Examples of such salts include sodium chloride, ammonium chloride, sodium citrate, potassium citrate, potassium chloride, magnesium chloride, calcium chloride, sodium phosphate, calcium phosphate, ammonium phosphate, magnesium phosphate, potassium phosphate, sodium sulfate, ammonium sulfate, potassium sulfate, magnesium sulfate, calcium sulfate, etc. Preferred salts herein are chlorides or sulfates. The most preferred salt herein is sodium chloride.

As used herein, the phrasing "copper or manganese salt" refers to a salt of copper or manganese with any anion, including organic anions, that is responsible for promoting oxidation of cysteine residues. Suitable anions include sulfates and chlorides, with copper chloride being particularly preferred. The copper or manganese may be added exogenously or may be residual from the fermentation or otherwise already present in the solution containing the polypeptide of interest.

B. Modes for Carrying Out the Invention

The invention herein concerns a method for increasing refolding yields of polypeptide from cellular hosts employing a minimal amount of copper or manganese salt as catalyst in a buffer. This buffer is at a pH of about 7 to 12, depending mainly on the type of polypeptide and reducing agent, preferably about 8 to 11, more preferably pH 8.5 to 11, and most preferably 8.5 to 10.5.

One key ingredient of the buffer is an alcoholic or polar aprotic solvent at a concentration of about 5–40% (v/v), preferably 10 to 30% (volume/volume) of the solution, depending, e.g., on the type of polypeptide and solvent, and the concentration of chaotropic agent. It is most preferably at a concentration of about 20% (v/v).

A second key ingredient to this buffer is an alkaline earth, alkali metal, or ammonium salt, which is present in a concentration of about 0.2 to 3M, preferably 0.2 to 2M, depending mainly on the chaotrope concentration, solvent concentration, and the type of alkaline earth, alkali metal, or ammonium salt and polypeptide employed. For example, if the cation is sodium, potassium, or ammonium, the concentration is about 0.5 to 3M, but if the cation is magnesium, the concentration is about 0.2 to 1M.

A third key ingredient of the buffer is an effective amount of a chaotropic agent. The amount of such chaotrope will depend mainly on the concentration of alkaline earth, alkali metal, or ammonium salt, the concentration of solvent, the specific type of alkaline earth, alkali metal, or ammonium salt employed, the specific type of chaotropic agent employed, and the type of polypeptide, as well as the pH of the buffer, but in general will range from about 0.1 to 9M, preferably about 0.5 to 6M, and most preferably about 1.5 to 4M. As to specific chaotropes, preferably about 0.1 to 2M of guanidine hydrochloride, and preferably about 1–3M, more preferably about 1–2.5M, and most preferably about 2M, of urea is utilized.

A fourth key ingredient of the buffer is an effective amount of a transition metal salt selected from copper and manganese salts so that oxidation and resultant refolding will occur. The amount of copper or manganese salt depends mainly on the type of transition metal and polypeptide employed and the oxygen level present. The lower the rate of oxygen addition or the oxygen level, the higher the amount of copper or manganese salt that can be employed. The copper or manganese salt concentration is typically about 0.01 to 15 μM, preferably about 0.01 to 10 μM, more preferably about 0.01 to 5 μM, and even more preferably about 0.01 to 0.5 μM. The above preferred ranges are particularly preferred for IGF-I. If the concentration is increased beyond about 15 μM, unexpectedly the yield of correctly folded polypeptide decreases dramatically. Most preferably, the concentration of a copper or manganese salt is about 0.5 μM. The transition metal salt may already be present in the buffer without addition of exogenous transition metal salt, for example, if it is residual from the fermentation, or it may be added to the buffer, or both.

Suitable host cells for expressing the DNA encoding the desired polypeptide are the prokaryote, yeast, or higher eukaryote cells. Suitable prokaryotes for this purpose include bacteria such as archaebacteria and eubacteria. Preferred bacteria are eubacteria, such as Gram-negative or Gram-positive organisms, for example, Enterobacteriaceae such as Escherichia, e.g., *E. coli*, Enterobacter, Erwinia, Klebsiella, Proteus, Salmonella, e.g., *Salmonella typhimurium*, Serratia, e.g., *Serratia marcescans*, and Shigella; Bacilli such as *B. subtilis* and *B. licheniformis* (e.g., *B. licheniformis* 41P disclosed in DD 266,710 published Apr. 12, 1989); Pseudomonas such as *P. aeruginosa*, Streptomyces; Azotobacter; Rhizobia; Vitreoscilla; and Paracoccus. Suitable *E. coli* hosts include *E. coli* W3110 (ATCC 27,325), *E. coli* 294 (ATCC 31,446), *E. coil* B, and *E. coli* X1776 (ATCC 31,537). These examples are illustrative rather than limiting.

Mutant cells of any of the above-mentioned bacteria may also be employed. It is, of course, necessary to select the appropriate bacteria taking into consideration replicability of the replicon in the cells of a bacterium. For example, *E. coli*, Serratia, or Salmonella species can be suitably used as the host when well known plasmids such as pBR322, pBR325, pACYA177, or pKN410 are used to supply the replicon.

*E. coli* strain W3110 is a preferred host or parent host because it is a common host strain for recombinant DNA product fermentations. Preferably, the host cell should secrete minimal amounts of proteolytic enzymes. For example, strain W3110 may be modified to effect a genetic mutation in the genes encoding proteins, with examples of such hosts including *E. coli* W3110 strain 27C7. The complete genotype of 27C7 is tonAΔ ptr3 phoAΔE15 Δ(argF-lac)169 ompTΔ degP41kan'. Strain 27C7 was deposited on Oct. 30, 1991 in the American Type Culture Collection as ATCC No. 55,244. Alternatively, the strain of *E. coli* having mutant periplasmic protease disclosed in U.S. Pat. No. 4,946,783 issued Aug. 7, 1990 may be employed. Alternatively, in vitro methods of cloning, e.g., PCR or other nucleic acid polymerase reactions, are suitable.

For example, strain W3110 may be modified to effect a genetic mutation in the genes encoding proteins endogenous to the host, with examples of such hosts including *E. coli* W3110 strain 1A2, which has the complete genotype tonAΔ; *E. coli* W3110 strain 9E4, which has the complete genotype tonAΔ ptr3; *E. coli* W3110 strain 27C7 (ATCC 55,244), which has the complete genotype tonAΔ ptr3 phoAΔE15 (argF-lac)169 ompTΔ degP41kan'; *E. coli* W3110 strain 37D6, which has the complete genotype tonAΔ ptr3 phoAΔE15 Δ(argF-lac)169 ompTΔ degP41kan' rbs7Δ ilvG; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued Aug. 7, 1990.

In addition to prokaryotes, eukaryotic microbes such as filamentous fungi or yeast are suitable cloning or expression hosts for polypeptide-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe* [Beach and Nurse, *Nature*, 290: 140 (1981); EP 139,383 published May 2, 1985]; Kluyveromyces hosts (U.S. Pat. No. 4,943,529; Fleer et al., supra) such as, e.g., *K. lactis* [MW98-8C, CBS683, CBS4574; Louvencourt et al., *J. Bacteriol.*, 737 (1983)], *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., supra), *K. thermotolerans*, and *K. marxianus*; yarrowia [EP 402,226]; *Pichia pastoris* [EP 183,070; Sreekrishna et al., *J. Basic Microbiol.*, 28: 265-278 (1988)]; Candida; *Trichoderma reesia* [EP 244,234]; *Neurospora crassa* [Case et al., *Proc. Natl. Acad. Sci. USA*, 76: 5259-5263 (1979)]; Schwanniomyces such as *Schwanniomyces occidentalis* [EP 394,538 published Oct. 31, 1990]; and filamentous fungi such as, e.g., Neurospora, Penicillium, Tolypocladium [WO 91/00357 published Jan. 10, 1991], and Aspergillus hosts such as *A. nidulans* [Ballance et al., *Biochem. Biophys. Res. Commun.*, 112: 284-289 (1983); Tilburn et al., *Gene*, 26: 205-221 (1983); Yelton et al., *Proc. Natl. Acad. Sci. USA*, 81: 1470-1474 (1984)] and *A. niger* [Kelly and Hynes, *EMBO J.*, 4: 475-479 (1985)].

Suitable host cells appropriate for the expression of the DNA encoding the desired polypeptide may also be derived from multicellular organisms. Such host cells are capable of complex processing and glycosylation activities. In principle, any higher eukaryotic cell culture is suitable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. See, e.g., Luckow et al., *Bio/Technology*, 6: 47-55 (1988); Miller et al., in *Genetic Engineering*, Setlow, J. K. et al., eds., Vol. 8 (Plenum Publishing, 1986), pp. 277-279; and Maeda et al., *Nature*, 315: 592-594 (1985). A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens*, which has been previously manipulated to contain the DNA encoding the desired polypeptide. During incubation of the plant cell culture with *A. tumefaciens*, the DNA encoding the desired polypeptide is transferred to the plant cell host such that it is transfected, and will, under appropriate conditions, express the DNA encoding the desired polypeptide. In addition, regulatory and signal sequences compatible with plant cells are available, such as the nopaline synthase promoter and polyadenylation signal sequences. Depicker et al., *J. Mol. Appl. Gen.*, 1: 561 (1982). In addition, DNA segments isolated from the upstream region of the T-DNA 780 gene are capable of activating or increasing transcription levels of plant-expressible genes in recombinant DNA-containing plant tissue. EP 321,196 published Jun. 21, 1989.

Examples of useful mammalian host cell lines are monkey kidney Cv1 line transformed by SV40 (COS-7, ATCC CRL 1651); human embryonic kidney line (293 or 293 cells subcloned for growth in suspension culture, Graham et al., *J. Gen Virol.*, 36: 59 [1977]); baby hamster kidney cells (BHK, ATCC CCL 10); Chinese hamster ovary cells/-DHFR (CHO, Urlaub and Chasin, *Proc. Natl. Acad. Sci. USA*, 77: 4216 [1980]); mouse sertoli cells (TM4, Mather, *Biol. Reprod.*, 23: 243-251 [1980]); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.*, 383: 44–68 [1982]); MRC 5 cells; FS4 cells; and a human hepatoma line (Hep G2).

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., *Molecular Cloning: A Laboratory Manual* [New York: Cold Spring Harbor Laboratory Press, 1989], or electroporation is generally used for prokaryotes or other cells that contain substantial cell-wall barriers. Infection with *Agrobacterium tumefaciens* is used for transformation of certain plant cells, as described by Shaw et al., *Gene*, 23: 315 (1983) and WO 89/05859 published Jun. 29, 1989. In addition, plants may be transformed using ultrasound treatment as described in WO 91/00358 published Jan. 10, 1991.

For mammalian cells without such cell walls, the calcium phosphate precipitation method of Graham and van der Eb, *Virology*, 52: 456–457 (1978) is preferred. General aspects of mammalian cell host system transformations have been described by Axel in U.S. Pat. No. 4,399,216 issued Aug. 16, 1983. Transformations into yeast are typically carried out according to the method of Van Solingen et al., *J. Bact.*, 130: 946 (1977) and Hsiao et al., *Proc. Natl. Acad. Sci. (USA)*, 76: 3829 (1979). However, other methods for introducing DNA into cells, such as by nuclear microinjection, electroporation, bacterial protoplast fusion with intact cells, or polycations, e.g., polybrene, polyornithine, etc., may also be used. For various techniques for transforming mammalian cells, see Keown et al., *Methods in Enzymology* (1989), Keown et al., *Methods in Enzymology* (1990) Vol. 185, pp. 527–537, and Mansour et al., *Nature*, 336: 348–352 (1988).

If prokaryotic cells are used to produce the polypeptide of interest in accordance with the method of this invention, they are cultured in suitable media in which the promoter can be constitutively or artificially induced as described generally, e.g., in Sambrook et al., *Molecular Cloning: A Laboratory Manual* (Cold Spring Harbor Laboratory Press, N.Y. 1989). Examples of suitable media are given below in the example section.

Any necessary supplements besides carbon, nitrogen, and inorganic phosphate sources may also be included at appropriate concentrations introduced alone or as a mixture with another supplement or medium such as a complex nitrogen source. The pH of the medium may be any pH from about 5–9, depending mainly on the host organism.

If mammalian host cells are used to produce the polypeptide of this invention, they may be cultured in a variety of media. Commercially available media such as Ham's F10 (Sigma), Minimal Essential Medium ([MEM], Sigma), RPMI-1640 (Sigma), and Dulbecco's Modified Eagle's Medium ([DMEM], Sigma) are suitable for culturing the host cells. In addition, any of the media described in Ham and Wallace, *Meth. Enz.*, 58: 44 (1979), Barnes and Sato, *Anal. Biochem.*, 102: 255 (1980), U.S. Pat. Nos. 4,767,704; 4,657,866; 4,927,762; or 4,560,655; WO 90/03430; WO 87/00195; U.S. Pat. Re. No. 30,985; or U.S. Pat. No. 5,122,469, the disclosures of all of which are incorporated herein by reference, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In general, principles, protocols, and practical techniques for maximizing the productivity of in vitro mammalian cell cultures can be found in *Mammalian Cell Biotechnology: A Practical Approach*, M. Butler, ed. (IRL Press at Oxford University Press, Oxford, 1991).

The above process can be employed whether the polypeptide is intracellular or in the periplasmic space. The preferred conditions given herein for isolating a polypeptide are directed particularly to inclusion bodies located in the periplasmic space.

It is often preferred to purify the polypeptide of interest from recombinant cell proteins or polypeptides to obtain preparations that are substantially homogeneous as to the polypeptide of interest before refolding. In one embodiment, as a first step, the culture medium or lysate is centrifuged to remove particulate cell debris. The membrane and soluble protein fractions may then be separated if necessary. The polypeptide may then be purified from the soluble protein fraction and from the membrane fraction of the culture lysate, depending on whether the polypeptide is membrane bound, is soluble, or is present in an aggregated form. The polypeptide thereafter is solubilized and then subsequently refolded using an appropriate buffer. The details for this first method of isolation are described below.

Insoluble, non-native polypeptide is isolated from the prokaryotic host cells in a suitable isolation buffer by any appropriate technique, e.g., one involving exposing the cells to a buffer of suitable ionic strength to solubilize most host proteins, but in which aggregated polypeptide is substantially insoluble, disrupting the cells so as to release the inclusion bodies and make them available for recovery by, for example, centrifugation. This technique is well known, and is described, for example, in U.S. Pat. No. 4,511,503.

Briefly, the cells are suspended in the buffer (typically at pH 5 to 9, preferably about 6 to 8, using an ionic strength of about 0.01 to 2M, preferably 0.1 to 0.2M). Any suitable salt, including sodium chloride, is useful to maintain a sufficient ionic strength value. The cells, while suspended in this buffer, are then disrupted by lysis using techniques commonly employed such as, for example, mechanical methods, e.g., a Manton-Gaulin press, a French press, or a sonic oscillator, or by chemical or enzymatic methods.

Examples of chemical or enzymatic methods of cell disruption include spheroplasting, which entails the use of lysozyme to lyse the bacterial wall [Neu et al., *Biochem. Biophys. Res. Comm.,* 17: 215 (1964)], and osmotic shock, which involves treatment of viable cells with a solution of high tonicity and with a cold-water wash of low tonicity to release the polypeptides [Neu et al., *J. Biol. Chem.,* 240: 3685–3692 (1965)]. A third method, described in U.S. Pat. No. 4,680,262 issued Jul. 14, 1987, involves contacting the transformed bacterial cells with an effective amount of a lower alkanol having 2 to 4 carbon atoms for a time and at a temperature sufficient to kill and lyse the cells.

After the cells are disrupted, the suspension is typically centrifuged to pellet the inclusion bodies. In one embodiment, this step is carried out at about 500 to 15,000 x g, preferably about 12,000 x g, in a standard centrifuge for a sufficient time that depends on volume and centrifuge design, usually about 10 minutes to 0.5 hours. The resulting pellet contains substantially all of the insoluble polypeptide fraction, but if the cell disruption process is not complete, it may also contain intact cells or broken cell fragments. Completeness of cell disruption can be assayed by resuspending the pellet in a small amount of the same buffer solution and examining the suspension with a phase contrast microscope. The presence of broken cell fragments or whole cells indicates that additional disruption is necessary to remove the fragments or cells and the associated non-refractile polypeptides. After such further disruption, if required, the suspension is again centrifuged and the pellet recovered, resuspended, and analyzed. The process is repeated until visual examination reveals the absence of broken cell fragments in the pelleted material or until further treatment fails to reduce the size of the resulting pellet.

In an alternative embodiment, the polypeptide of interest, preferably exogenous, is isolated by solubilization in a suitable buffer. This procedure can be in-situ solubilization involving direct addition of reagents to the fermentation vessel after the polypeptide has been produced recombinantly, thereby avoiding extra steps of harvesting, homogenization, and centrifugation to obtain the polypeptide. The remaining particulates can be removed by centrifugation or filtration, or combinations thereof. Alternatively, and more preferably, one may use a multiple-phase isolation/extraction system for purifying polypeptides from the remaining particulates.

In the aqueous multiple-phase isolation system, one or more denaturants (chaotropic agent), such as urea, guanidine hydrochloride, and/or a base, and a reducing agent, such as dithiothreitol or cysteine, are added to the polypeptide-containing medium at basic pH and then phase-forming species are added to the broth. Once this second group of reagents is added to the broth, multiple phases are formed whereby one phase is enriched in the polypeptide and depleted in biomass solids and nucleic acids. Preferably, the system has two to four phases, and more preferably two phases, one being enriched in polypeptide and the other being enriched in biomass solids and nucleic acids. Preferably, the desired polypeptide partitions to the upper phase so that the upper phase is enriched in the polypeptide and depleted in the biomass solids and nucleic acids.

Thus, after fermentation is complete, the cell culture is contacted with one or more chaotropic agents, an optional reducing agent, and phase-forming reagents so that multiple phases are formed, one phase of which is enriched in the polypeptide of interest. It is preferred to add the chaotrope and reducing agent first to extract the polypeptide from the cell and maintain its solubility in the broth before the phase-forming reagents are added. Also, while the polypeptide of interest can be extracted from (and enriched in) any phase, preferably it is recovered from the uppermost phase.

Most preferably, the chaotropic agent and optional reducing agent are added directly to the fermentation broth in the fermentation vessel before isolation of the polypeptide so that the reagents permeate the cells and the polypeptide is solubilized and diffuses to the surrounding medium.

Examples of suitable reducing agents include dithiothreitol (DTT), β-mercaptoethanol (BME), cysteine, thioglycolate, and sodium borohydride. The amount of reducing agent to be present in the buffer will depend mainly on the type of reducing agent and chaotropic agent, the type and pH of the buffer employed, and the type and concentration of the polypeptide in the buffer. An effective amount of reducing agent is that which is sufficient to eliminate intermolecular disulfide-mediated aggregation. For example, with 0.5–6 mg/mL IGF-I in a buffered solution at pH 7.5–10.5 containing 1–4M urea, the DTT concentration is at about 1–20 mM, and the concentration of cysteine is at about 10–50 mM. The preferred reducing agent is DTT at about 2–10 mM or cysteine at about 30–50 mM.

Chaotropic agents suitable for practicing this invention include, e.g., urea and salts of guanidine or thiocyanate, more preferably urea, guanidine hydrochloride, or sodium thiocyanate. The amount of chaotropic agent necessary to be present in the buffer depends, for example, on the type of chaotropic agent and polypeptide present. The amount of chaotropic agent to be added to the fermentation broth will be sufficiently high to extract the polypeptide from the cell and maintain its solubility in the broth. If the polypeptide is to be extracted from the top phase, the amount of chaotropic agent must be sufficiently low so that after addition of the phase-forming species, the density is not increased to a point where the solids rise to the top instead of settling to the bottom. Generally the concentration of chaotropic agent is about 0.1 to 9M, preferably about 0.5–9M, more preferably about 0.5 to 6M, and most preferably about 0.5–3M. Also, preferably the chaotropic agent is added to the culture medium before the phase-forming reagents are added. The preferred chaotropic agent herein is urea at about 1.5–2.5M, more preferably at about 2M, or guanidine hydrochloride at about 0.5–3M. Most preferably, the chaotropic agent is urea.

The concentration of the polypeptide in the aqueous solution to which the chaotrope and reducing agent are added must be such that the polypeptide will be recovered in the maximum yield. The exact amount to employ will depend, e.g., on the type of polypeptide and the concentrations and types of other ingredients in the aqueous solution, particularly the reducing agent, chaotropic agent, phase-forming species, and pH. For polypeptides in general, the preferred concentration of polypeptide is about 0.1 to 15 mg/mL. The preferred concentration of IGF-I (resulting in the maximum yield of denatured or non-native IGF-I) is in the range of 0.5–6 mg per mL, more preferably 1.5–5 mg/mL.

The types of phase-forming species to employ herein depend on many factors, including the type of polypeptide and the ingredients in the fermentation broth being treated. The species must be selected so that the polypeptide does not precipitate and one phase is more hydrophobic than the other phase so that the polypeptide will be located in the more hydrophobic phase and the biomass solids and nucleic acids will settle to the less hydrophobic phase.

The phase-forming species may be a combination of agents, including polymer combinations (polymer-polymer), polymer-salt combinations, solvent-salt, and polymer-solvent combinations. Suitable polymers are both highly hydrophilic polymers and less hydrophilic polymers, i.e., any phase-forming polymers that are known in the art. Examples include polyethylene glycol or derivatives thereof, including various molecular weights of PEG such as PEG 4000, PEG 6000, and PEG 8000, derivatives of PEG described, for example, in Grunfeld et al., supra, polyvinylpyrrolidone (PVP), in a preferable molecular weight range of about 36,000 to 360,000, starches such as dextran (e.g., dextran 70 and 500), dextrins, and maltodextrins (preferable molecular weight between about 600 and 5,000), sucrose, and Ficoll-400™ polymer (a copolymer of sucrose and epichlorohydrin). The preferred polymer herein is polyethylene glycol, polypropylene glycol, polyvinylpyrrolidone, or a polysaccharide such as a dextran. The most preferred polymer herein is PEG of different molecular weights or a PEG-polypropylene glycol combination or copolymer.

Examples of suitable organic solvents include ethylene glycol, glycerol, dimethyl sulfoxide, polyvinylalcohol, dimethylformamide, dioxane, and alcohols such as methanol, ethanol, and 2-propanol. Such solvents are such that, when added to aqueous solution, they increase the hydrophobicity of the solution.

The salts can be inorganic or organic and preferably do not act to precipitate the polypeptide. Salts containing transition elements are not preferred as they tend to precipitate the polypeptide. Anions are selected that have the potential for forming aqueous multiple-phase systems. Examples include ammonium sulfate, sodium dibasic phosphate, sodium sulfate, ammonium phosphate, potassium citrate, magnesium phosphate, sodium phosphate, calcium phosphate, potassium phosphate, potassium sulfate, magnesium sulfate, calcium sulfate, sodium citrate, manganese sulfate, manganese phosphate, etc. Types of salts that are useful in forming bi-phasic aqueous systems are evaluated more fully in Zaslavskii et al., *J. Chrom.*, supra. Preferred salts herein are sulfates, phosphates, or citrates and are alkali or alkaline earth metals. More preferred are sulfates and citrates, and most preferred are sulfates since there are fewer pH limitations with sulfates. The most preferred salts herein are sodium sulfate and sodium citrate.

The amounts of phase-forming species to add to the polypeptide of interest to obtain a satisfactory multiple-phase system are those known in the art. The amount of phase-forming species added to the polypeptide will depend on such factors as, for example, the amount of chaotropic agent and reducing agent, if any, already present in the fermentation broth, the nature of the cell culture media, the type of cells used in the fermentation, the type of polypeptide being treated, whether the polypeptide will be recovered from the lower or upper phase, and the type(s) of phase-forming species being added. The general concentration of polymer employed is about 5% (w/w) up to the limit of solubility for the polymer and the concentration of salt employed is about 3% (w/w) up to the limit of solubility for the salt, depending on the size of the phase-volume ratio needed. The phase-volume ratio must be sufficient to accomodate the biomass solids. The types and amounts of phase-forming species that are effective can be determined by phase diagrams and by evaluating the final result, i.e., the degree of purity and the yield of the polypeptide of interest. If the phase-forming species are a polymer-salt combination, preferably the concentration of salt added is about 4–15% (w/w) and the concentration of polymer is 5–18% (w/w) so that the desired polypeptide will be in an opposite phase from that in which the biomass solids and nucleic acids are present.

If the system desired is one where the polypeptide is distributed in the top phase and the biomass solids and nucleic acids are in the bottom phase, then there is a window of concentrations of phase-forming species. When higher amounts of chaotropic agent are added to maintain solubilization, the higher the amount of phase-forming species required. However, a high concentration of all these reagents will increase the density of the solution. A high density will cause the biomass solids to settle less readily. An overly high density will cause biomass solids to float on the surface. Hence, the concentrations of chaotropic agent and phase-forming species must be sufficiently high to maintain a fully solubilized polypeptide, but low enough to allow the biomass solids and nucleic acids to sediment to the opposite (lower) phase.

If the polypeptide is to be recovered in the upper phase, typically the salt concentration will be about 4–7% (w/w) and the polymer concentration will be about 12–18% (w/w), depending, e.g., on the type of salt, polymer, and polypeptide. If an organic solvent is added as a phase-forming species, such as ethanol, it is preferably added in an amount of about 10 to 30% (volume/volume) of the solution, depending, e.g., on the type of polypeptide and alcohol and if any other phase-forming species is present, preferably at a concentration of about 20% (v/v).

The exact conditions for contacting the cell culture with the various reagents will depend on, e.g., the pH of the buffer, the types of phase-forming reagents, and the types and concentrations of polypeptide and chaotropic and reducing agents. The reaction temperature is generally about 20–40° C., more preferably room temperature. The contacting step will generally be carried out for at least about 30 minutes, preferably about 30 minutes to 12 hours depending on whether side-reactions will occur, more preferably about 30 minutes to 8 hours, and most preferably about 30 minutes to 1.5 hours.

If the polypeptide is being unfolded, the degree of unfolding is suitably determined by chromatography of the non-native polypeptide, including hydrophobic interaction chromatography or ion-exchange chromatography. Increasing peak area for the non-native material indicates how much non-native polypeptide is present.

Once the multiple-phase system is established, one phase will be enriched in the polypeptide and depleted in the disrupted particles and cells comprising the biomass solids and nucleic acids. In a two-phase system, preferably the top phase is enriched in the polypeptide whereas the bottom phase is enriched in the disrupted particles and cells. The polypeptide can be easily recovered by separation of the phases. This recovery step may be accomplished by decanting the upper phase, by draining the lower phase, or by centrifugation. The polypeptide can then be isolated from the phase in which it is contained by changing the pH of the phase so as to precipitate the polypeptide or by adding a suitable solvent, whereupon the precipitated polypeptide is suitably recovered by centrifugation or filtration or as a slurry. Alternatively, the polypeptide can be recovered from the polymer-containing phase by re-extraction by addition of a suitable polymer, salt, or solvent. In the case of IGF-I, the polypeptide is recovered from the isolated polymer phase by lowering the pH so that the IGF-I will precipitate, resulting in a yield of IGF-I of as much as or more than about 97%.

Once obtained from the liquid phase of the multiple-phase system, or at a later stage of purification, the polypeptide is suitably refolded into an active conformation using the invention described herein.

If the polypeptide is not already in soluble form before it is to be refolded, it may be solubilized by incubation in alkaline buffer containing chaotropic agent and reducing agent in amounts necessary to substantially solubilize the polypeptide. This incubation takes place under conditions of polypeptide concentration, incubation time, and incubation temperature that will allow solubilization of the polypeptide to occur in the alkaline buffer.

Measurement of the degree of solubilization of the polypeptide in the buffer is suitably carried out by turbidity determination, by analyzing polypeptide fractionation between the supernatant and pellet after centrifugation on reduced SDS gels, by protein assay (e.g., the Bio-Rad protein assay kit), or by HPLC.

The pH range of the alkaline buffer for solubilization typically is at least about 7.5, with the preferred range being about 8–11. Examples of suitable buffers that will provide a pH within this latter range include glycine, CAPSO (3-[Cyclohexylamino]-2-hydroxy-1-propanesulfonic acid), AMP (2-Amino-2-methyl-1-propanol), CAPS (3-[Cyclohexylamino]-1-propanesulfonic acid), CHES (2-[N-Cyclohexylamino]ethanesulfonic acid), and TRIS HCl (Tris [hydroxymethyl]aminomethane) hydrochloride. The preferred buffer herein is glycine or CAPSO, preferably at a concentration of about 20 mM, at a pH of about 8.5 to 11, preferably about 10–11.

The concentration of the polypeptide in the buffered solution for solubilization must be such that the polypeptide will be substantially solubilized or partially or fully reduced and denatured. Alternatively, the polypeptide may be initially insoluble. The exact amount to employ will depend, e.g., on the concentrations and types of other ingredients in the buffered solution, particularly the type of polypeptide employed, the type and amount of reducing agent, the type and amount of chaotropic agent, and the pH of the buffer. For example, the concentration of IGF-I may be increased at least three-fold if the concentration of reducing agent, e.g., DTT, is concurrently increased, to maintain a ratio of DTT:IGF-I of from about 3:1 to 10:1. It is desirable to produce a more concentrated solubilized protein solution prior to dilution refolding. Thus, the preferred concentration of polypeptide is at least about 30 mg/mL, with a more preferred range of 30–50 mg per mL. For example, IGF-I may be solubilized to a concentration of about 30–50 mg/mL in 2M urea, 10 mM DTT and diluted to, for example, about 1 mg/mL for folding.

After the polypeptide is solubilized, it is placed or diluted into the buffer containing the solvent, chaotropic agent, and salts as described above. The buffer can be any of those listed above for the first buffered solution, with CAPSO, glycine, and CAPS being preferred at pH 8.5–11, particularly at a concentration of about 20 mM, and most preferably CAPSO and glycine. The polypeptide may be diluted with the refolding buffer, preferably at least five fold, more preferably at least about ten fold. Alternatively, the polypeptide may be dialyzed against the refolding buffer. The refolding is typically carried out at about 0°–45° C., preferably about 20°–40° C., more preferably about 23°–37° C., even more preferably about 25°–37° C., and most preferably about 25° C. for at least about one hour. The preferred temperature is not apparently affected by salt, solvent, and chaotropic agent levels, but may be affected by the presence of sucrose and glycerol, in which case it should be kept above about 20° C. The solution optionally also contains a reducing agent and an osmolyte.

The reducing agent is suitably selected from those described above for the solubilizing step in the concentration range given. Its concentration will depend especially on the concentrations of alkaline earth, alkali metal, or ammonium salt, polypeptide, and solvent. Preferably, the concentration of reducing agent is about 0.5 to 8 mM, more preferably about 1–5 mM, even more preferably about 0.5–2 mM. The preferred reducing agents are DTT and cysteine.

The optional osmolyte is preferably sucrose (in a concentration of about 0.25–1M) or glycerol (in a concentration of about 1–4M). More preferably, the sucrose concentration is at about 1M and the glycerol concentration is at about 4M.

The initial concentration of polypeptide in the folding buffer is such that the ratio of correctly folded to misfolded conformer recovered will be maximized, as determined by HPLC, RIA, or bioassay. The exact concentration will depend, for example, on the type of polypeptide employed. The preferred concentration of polypeptide (resulting in the maximum yield of correctly folded conformer) is in the range of about 0.1 to 15 mg/mL, more preferably about 0.1 to 6 mg/mL, and most preferably about 0.2 to 5 mg/mL.

In addition, a source of oxygen such as air or oxygen gas is entrained in or otherwise introduced into the buffer so as to effect oxidation together with the copper or manganese salt. The oxygen can be present in the buffer at any point in time, including before the polypeptide or any other reagents are added to the is buffer.

The amount of oxygen source introduced will depend, e.g., on the type of vessel utilized, the type and concentration of polypeptide, the type of oxygen source, the type and amount of copper or manganese salt, and the type and amount of reducing agent present, if any, and the type and amount of chaotropic agent present as well as the pH of the buffer. Generally, the oxygen source will be introduced by passive means (e.g., as air in head space in a ratio of air space to fluid volume of 2:1) using an agitator. Alternatively, the oxygen source may be introduced by bubbling through a sparger. The rate of introduction of the oxygen must be sufficient to allow folding to reach completion in preferably about 1 to 12 hours, more preferably about 1 to 6 hours, and most preferably about 1 to 3 hours. The addition of molar oxygen is proportional to the reductant concentration and polypeptide concentration, but inversely proportional to the copper or magnesium salt concentration. The rate of oxidation is limited by the level of catalyst, not by the oxygen addition rate. A higher sparging rate is required for larger volume folding.

The degree of refolding that occurs upon this second incubation is suitably determined by the RIA titer of the polypeptide or by HPLC analysis using e.g., a Vydac or Baker C-18 column, with increasing RIA titer or correctly folded polypeptide peak size directly correlating with increasing amounts of correctly folded, biologically active polypeptide conformer present in the buffer. The incubation is carried out to maximize the yield of correctly folded polypeptide conformer and the ratio of correctly folded polypeptide conformer to misfolded polypeptide conformer recovered, as determined by RIA or HPLC, and to minimize the yield of multimeric, associated polypeptide as determined by mass balance.

After the polypeptide is refolded, the following procedures are exemplary of suitable purification procedures for obtaining greater purity: fractionation on immunoaffinity or ion-exchange columns; ethanol precipitation; reverse phase HPLC; hydrophobic interaction chromatography; chromatography on silica or on an ion-exchange resin such as S-Sepharose and DEAE; chromatofocusing; SDS-PAGE; ammonium sulfate precipitation; and gel filtration using, for example, Sephadex G-75.

The invention will be more fully understood by reference to the following examples, which are intended to illustrate the invention but not to limit its scope. All literature and patent citations are expressly incorporated by reference.

EXAMPLE I

A. Construction of host cell strain 37D6

The host used to produce recombinant human IGF-I in the fermentation described in this example was a derivative of *E. coli* W3110, designated 37D6. The complete genotype of 37D6 is tonAΔ ptr3 phoAΔE15 Δrbs7 ilvG Δ(argF-lac)169 ompTΔ degP41kan$^r$. The derivation of strain 27C7, which is a parent strain for 37D6 having the genotype tonAΔ ptr3 phoAΔE15 Δ (argF-lac)169 ompTΔ degP41kan$^r$, is set forth in WO 93/11240 published Jun. 10, 1993, the disclosure of which is incorporated herein by reference. Strain 27C7 was deposited on Oct. 30, 1991 in the American Type Culture Collection as ATCC No. 55,244.

HaeII-EcoRI 196-bp fragment containing the IGF-I gene except the initial 5' end was isolated from plasmid p200. p200 is a pBR322-derived plasmid having, in the 5' to 3' order, the chelatin promoter, the MF alpha I prepro signal sequence, DNA encoding mature IGF-I, and the 2-micron terminator. It contains the ColE1 origin of replication for bacteria and the 2-micron origin for yeast. A restriction enzyme plasmid diagram of p200 is provided in FIG. 1. The nucleotide sequence (SEQ. ID NO. 1) of the EcoRI (starting at position 1149) to EcoRI (starting at position 1628) fragment of p200 containing the MF alpha I prepro and IGF-I gene is provided in FIG. 2. The HaeII, PstI, BamHI, and SalI restriction sites that are also in the diagram in FIG. 2 are indicated in the sequence by underlining. A piece of synthetic DNA linking the signal sequence to the IGF-I gene (NcoI to HaeII) was prepared having the following sequence:

```
5'-CATG GCC GGT CCG GAA ACT CTG TGC GGC GC    (SEQ. ID NO. 2)
3'-      CGG CCA GGC CTT TGA GAC ACG C         (SEQ. ID NO. 3).
```

Strain 37D6 is the same as 27C7 described above except for having a rbs7 deletion (ribose utilization minus) and having a restored ilvG locus. Both markers can be introduced by P1 transduction.

B. Description/Construction of IGF-I Expression Plasmid pBKIGF2B

In the IGF-I-expressing plasmid pBKIGF-2B, the transcriptional and translational sequences required for expression of the IGF-I gene in *E. coli* are provided by the alkaline phosphatase promoter and the trp Shine-Dalgarno sequence. The lambda $t_o$ transcriptional terminator is situated adjacent to the IGF-I termination codon. Secretion of the protein from the cytoplasm is directed by the lamB signal sequence or alternatively by the STII signal sequence. The majority of rhIGF-I is found in the cell periplasmic space. Plasmid pBKIGF-2B confers tetracycline resistance upon the transformed host.

Plasmid pBKIGF-2B was constructed in several steps using as intermediate plasmids pLS32Tsc, pLBIGFTsc, pLS33Tsc, and pRanTsc.

Step 1: pLS32Tsc

The secretion plasmid pLS32Tsc contains the IGF-I gene. The transcriptional and translational sequences required for expression of the IGF-I gene in *E. coli* are provided by the alkaline phosphatase promoter and the trp Shine-Dalgarno sequence. The lambda $t_o$ transcriptional terminator is situated adjacent to the IGF-I termination codon. Secretion of the protein from the cytoplasm is directed by the lamb signal sequence or alternatively the STII signal sequence. The majority of rhIGF-I is found in the cell periplasmic space. Plasmid pLS32Tsc confers tetracycline resistance upon the transformed host.

Plasmid pLS32Tsc was constructed in several steps using as intermediate plasmids pLS32, pAPlamB, pLS321amB, pLS331amB, and pLS33Tsc as disclosed in detail in WO 93/11240, supra.

Step 2: pLBIGFTsc

Step a: pLamBIGF

Figure 3:
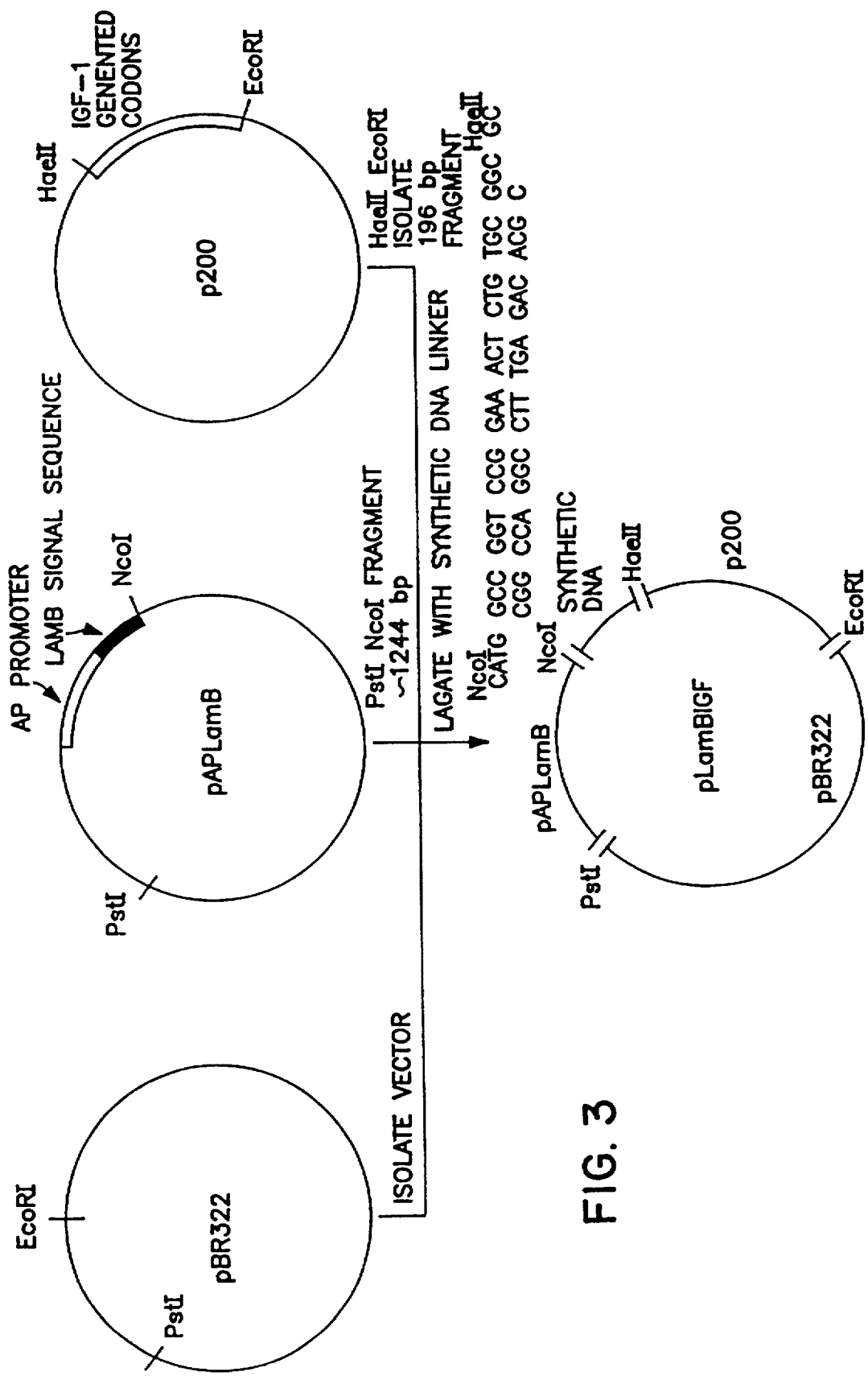
FIG. 3 depicts the construction of pLamBIGF from three plasmid fragments and a piece of synthetic DNA (SEQ. ID NOS. 2 and 3). pLamBIGF is an intermediate plasmid in the production of pLBIGFTsc, used to prepare pBKIGF-2.

For the first part of the ligation, the EcoRI-PstI vector fragment from pBR322 was isolated. For the second part of the ligation, a PstI-NcoI 1244-bp fragment was isolated from pAPLamB. For the third part of the ligation, the The three plasmid fragments and the synthetic DNA were ligated together to form pLamBIGF, as shown in FIG. 3.

Step b: pLBIGFTsc

Figure 4:
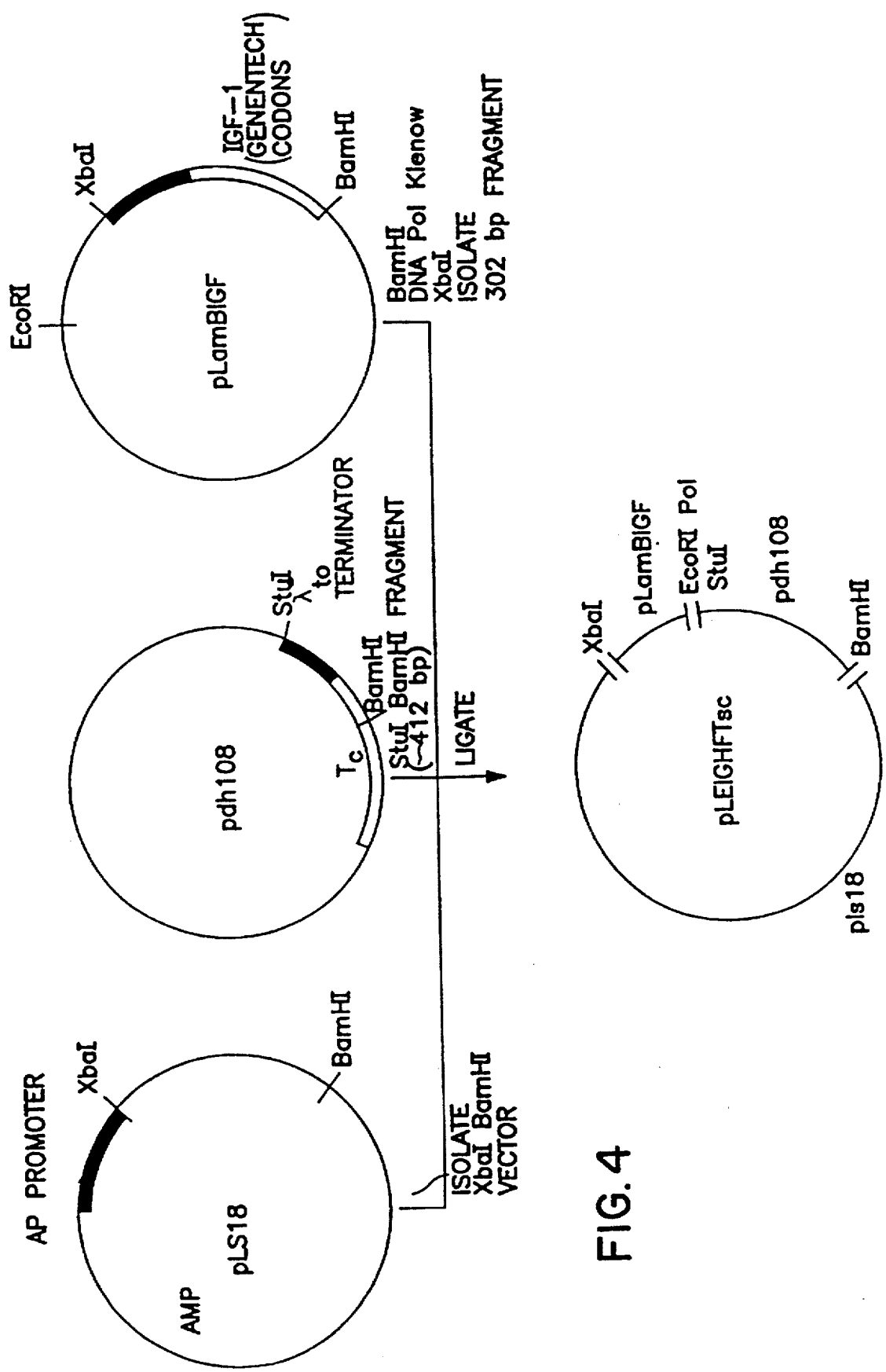
FIG. 4 depicts the construction of the intermediate plasmid pLBIGFTsc from pLamBIGF.

The XbaI-BamHI vector fragment was isolated from pLS18 as the first ligation fragment. The second part of the ligation was a 412-bp StuI-BamHI fragment from the plasmid pdH108-4 described above. The third part of the ligation was prepared by an EcoRI digest of pLamBIGF, followed by treatment with DNA polymerase Klenow fragment, followed by a XbaI digest. The resultant 302-bp fragment was isolated. These three fragments were ligated to yield pLBIGFTsc, as shown in FIG. 4.

Step 3: pRanTsc

Figure 5:
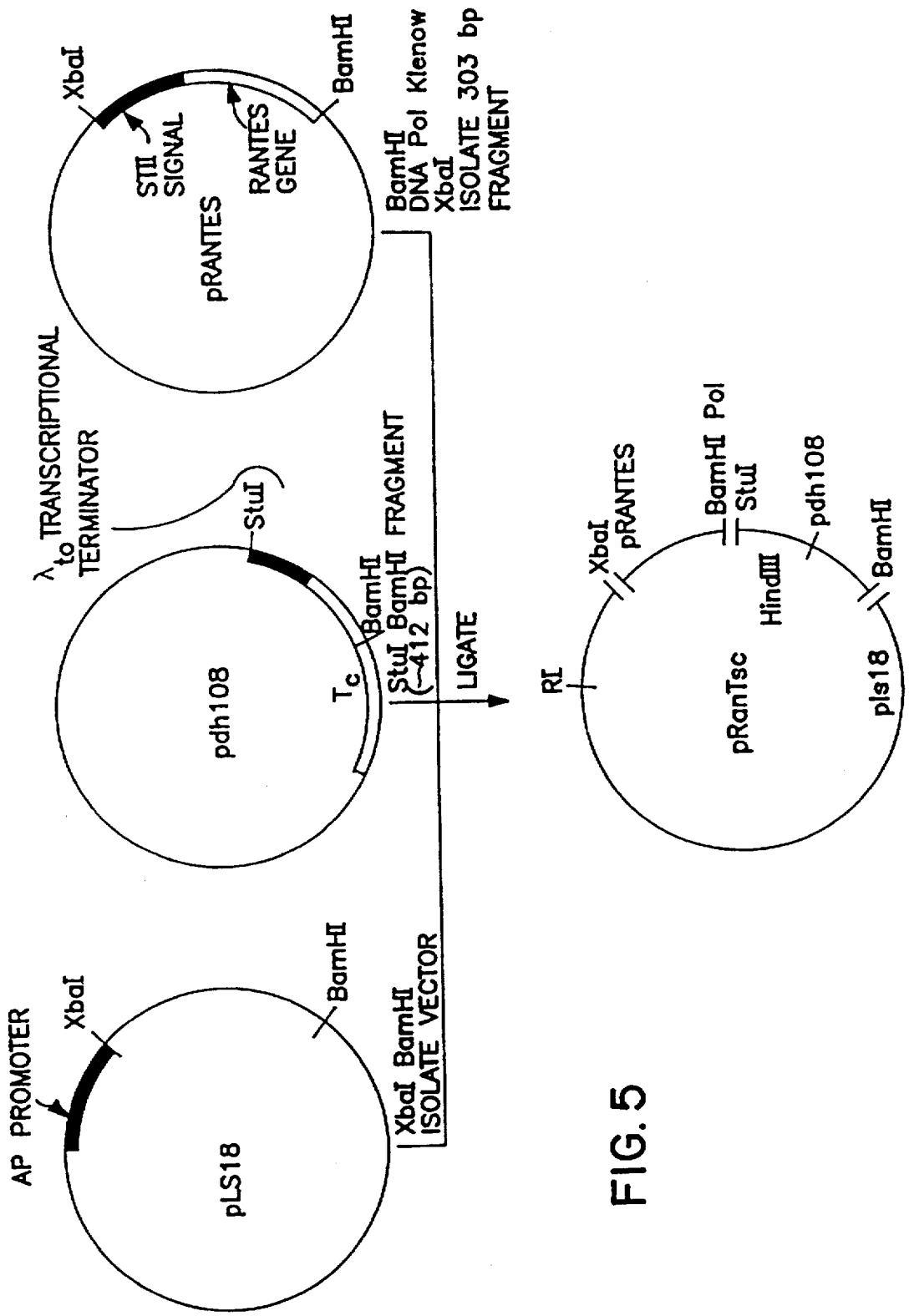
FIG. 5 depicts the construction of the intermediate plasmid pRanTsc used in the production of pBKIGF-2.

The XbaI-BamHI vector fragment from pLS18 was isolated as the first ligation fragment. The second part of the ligation was a 412-bp StuI-BamHI fragment from the plasmid pdH108-4 described above. The third part of the ligation was prepared from pRANTES. pRANTES is a pBR322-based plasmid containing a fragment of a XbaI linker followed by the STII signal, followed by the cDNA encoding RANTES [as published by Schall et al., *J. Immunol.*, 141: 1018 (1988)], followed by the BamHI linker. The third fragment was prepared by digestion of pRANTES with BamHI, followed by treatment with DNA polymerase Klenow fragment, followed by a XbaI digest. The resultant 303-bp fragment was isolated. These three fragments were ligated to yield pRanTsc, as shown in FIG. 5.

Step 4: pBKIGF-2

Figure 6:
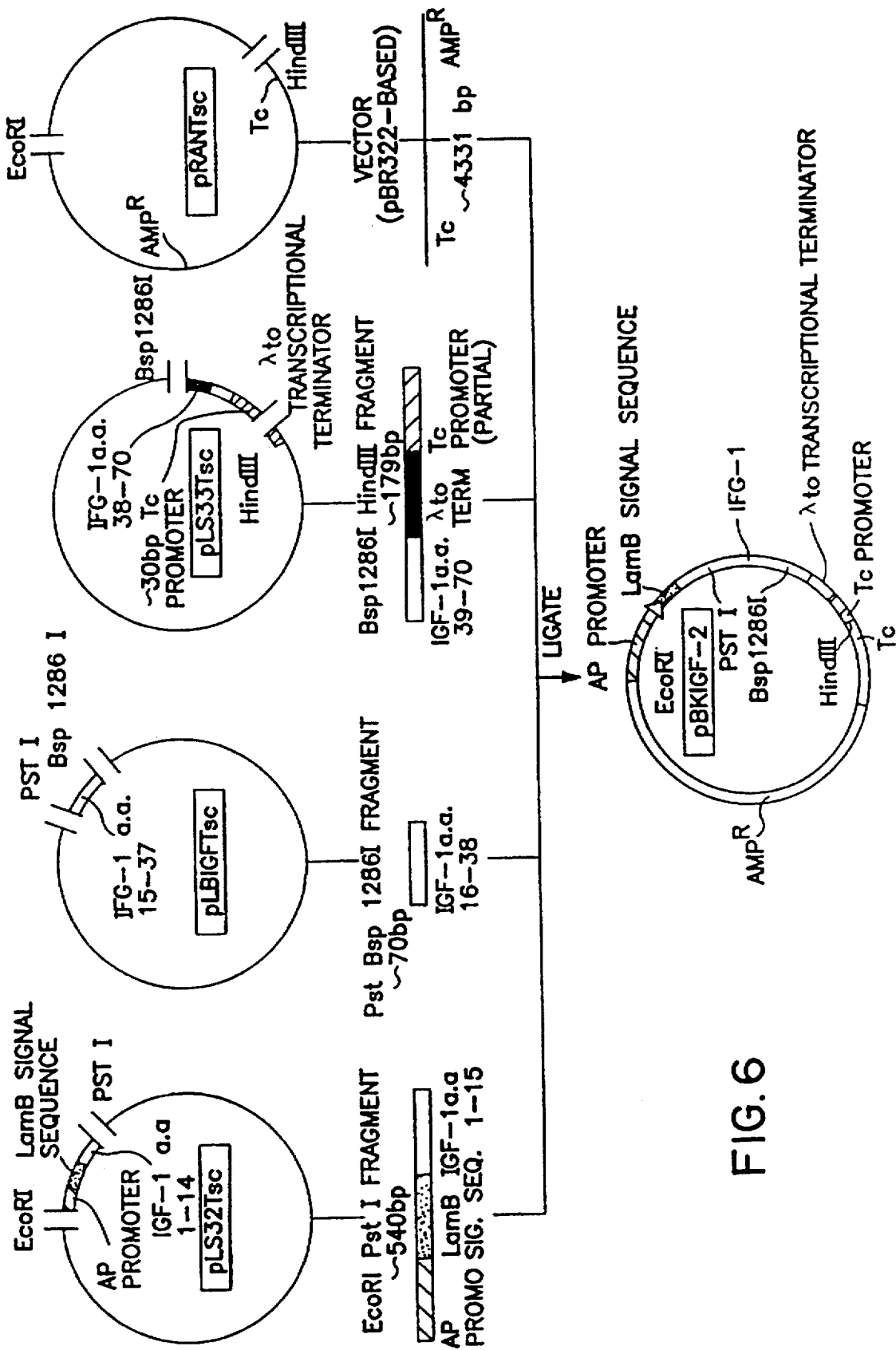
FIG. 6 depicts the construction of pBKIGF-2 from pLS32Tsc, pLBIGFTsc, pLS33Tsc, and pRanTsc.

As shown in FIG. 6, the EcoRI-PstI 540-bp fragment containing the alkaline phosphatase promoter, the lamB signal sequence, and DNA encoding the first 15 amino acids of IGF-I was excised from pLS32Tsc. The Pst-Bsp1286I fragment (~70 bp) containing DNA encoding amino acids 16–38 of IGF-I was excised from pLBIGFTsc. The Bsp1286I-HindIII (~179-bp) fragment containing DNA encoding amino acids 39–70 of IGF-I, the lambda terminator, and the Tc promoter was excised from pLS33Tsc. Finally, the EcoRI-HindIII ~4331-bp vector fragment (pBR322-based) was excised from pRanTsc. These four fragments were ligated to give pBKIGF-2, which contains the AP promoter, the lamB signal sequence, the DNA encoding the entire IGF-I protein, the transcriptional terminator, the Tc promoter, and the tetracycline and ampicillin resistance markers.

Step 5: pBKIGF-2A pBKIGF-2 was digested with PstI and ClaI and the ~245-bp fragment was isolated. This contains amino acids 16–70 of IGF-I and the lambda $t_o$ terminator. pLBIGFTsc was digested with NcoI and ClaI and the vector fragment was isolated. This vector fragment contains the AP promoter, the lamB signal, and the Tet$^r$ gene. These two fragments were ligated to a piece of synthetic DNA that replaces the 5' end of IGF-I DNA from NcoI to PstI with synthetically derived codons as follows:

```
5'- CATGGCC GGT CCC GAA ACT CTG TGC GGT GCT GAA CTG GTT GAC GCT CTG CA-3'
3'-      CGG CCA GGG CTT TGA GAC ACG CCA CGA CTT GAC CAA CTG CGA G-5'
```

(SEQ. ID NOS. 4 and 5, respectively).

Figure 7:
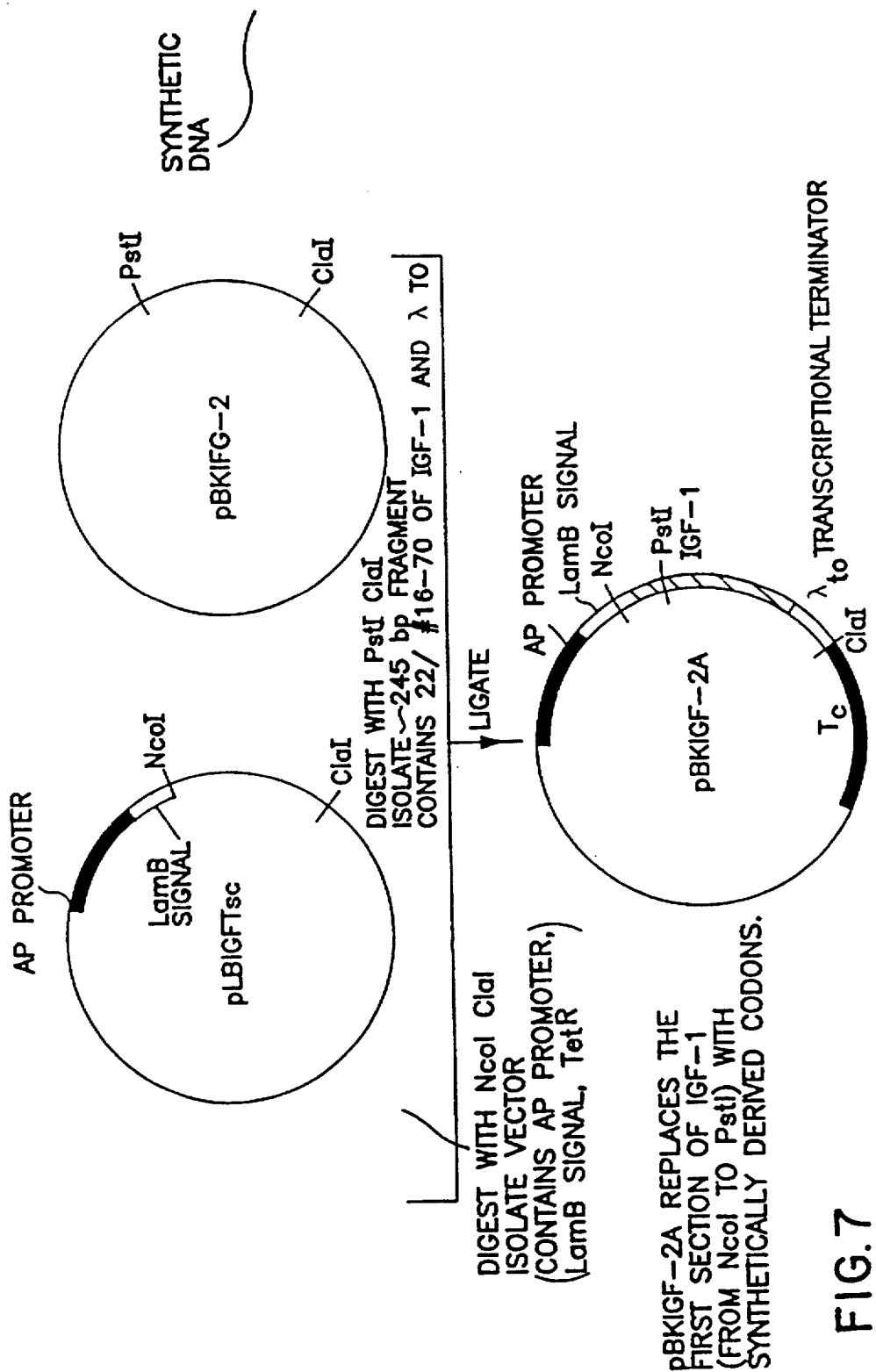
FIG. 7 depicts the construction of pBKIGF-2A, used to prepare pBKIGF-2B, from pLBIGFTsc, pBKIGF-2, and a piece of synthetic DNA (SEQ. ID NOS. 4 and 5).

The resulting plasmid was designated pBKIGF-2A. The construction is shown in FIG. 7.

Step 6: pLamBRan

This plasmid was prepared by digesting pLS33LamB with NcoI and BamHI and the vector fragment was isolated. pLS33LamB is a plasmid made from pBR322 into which was inserted the AP promoter, the lamB signal, and the IGF-I gene. BamHI cuts in the Tc portion of the plasmid and NcoI cuts at the 5' end of the IGF-I gene. The second fragment was generated by digesting pRANTES with BsaJI and BamHI and isolating the resultant ~200-bp fragment. The third fragment was a piece of synthetic DNA to link the RANTES gene with the signal sequence from NcoI to BsaJI. This synthetic DNA has the sequence:

```
       NcoI                  BsaJI
5'-CATGGCCTCCCCATATTC-3'
   3' - CGGAGGGGTATAAGGAGC-5'
```

(SEQ. ID NOS. 6 and 7, respectively).

Figure 8:
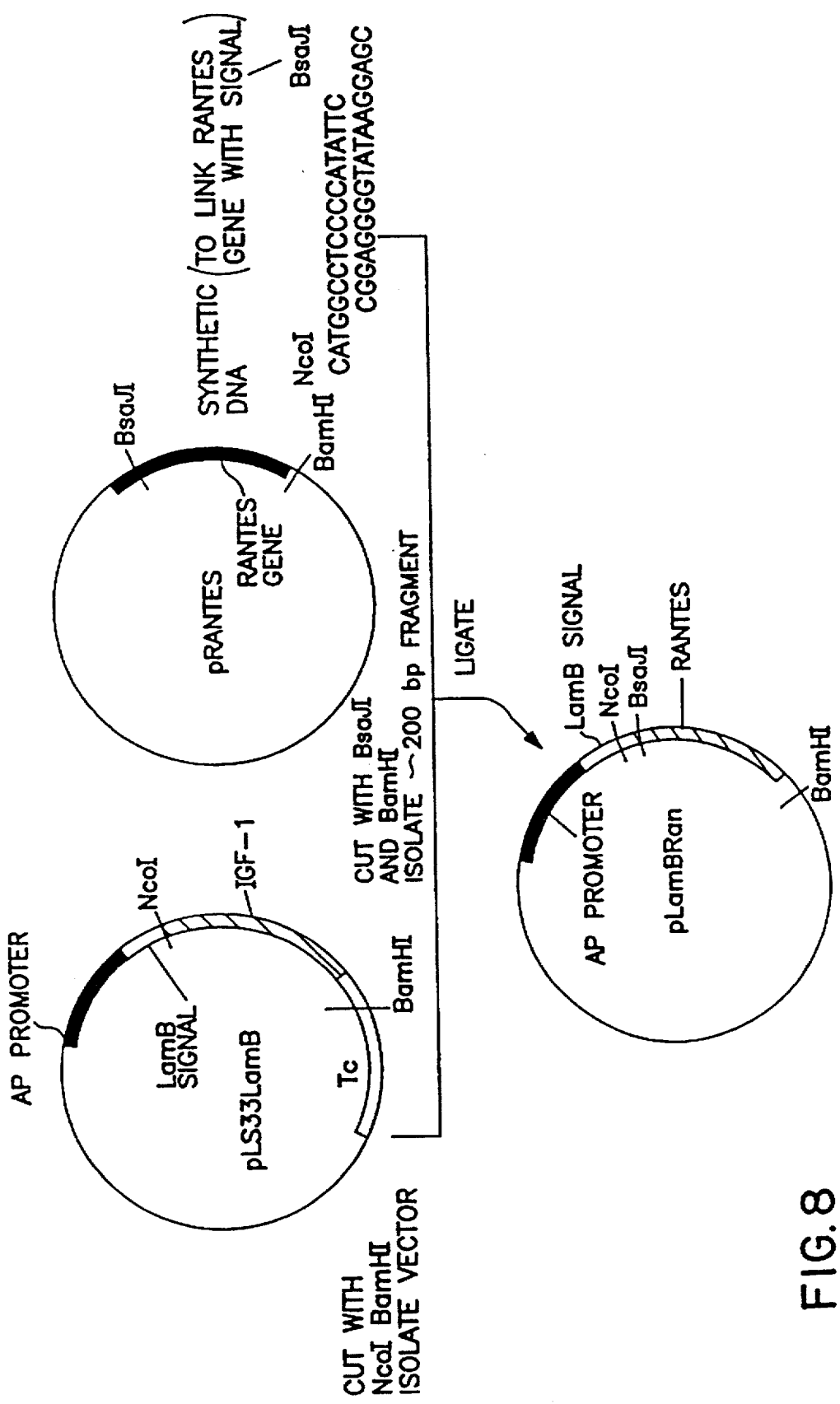
FIG. 8 depicts the construction of pLamBRan, used to prepare pBKIGF-2B, from pLS33LamB, pRANTES and a piece of synthetic DNA (SEQ. ID NOS. 6 and 7).

The resulting vector was named pLamBRan, and its construction is shown in FIG. 8.

Step 7: pBKIGF-2B

Figure 9:
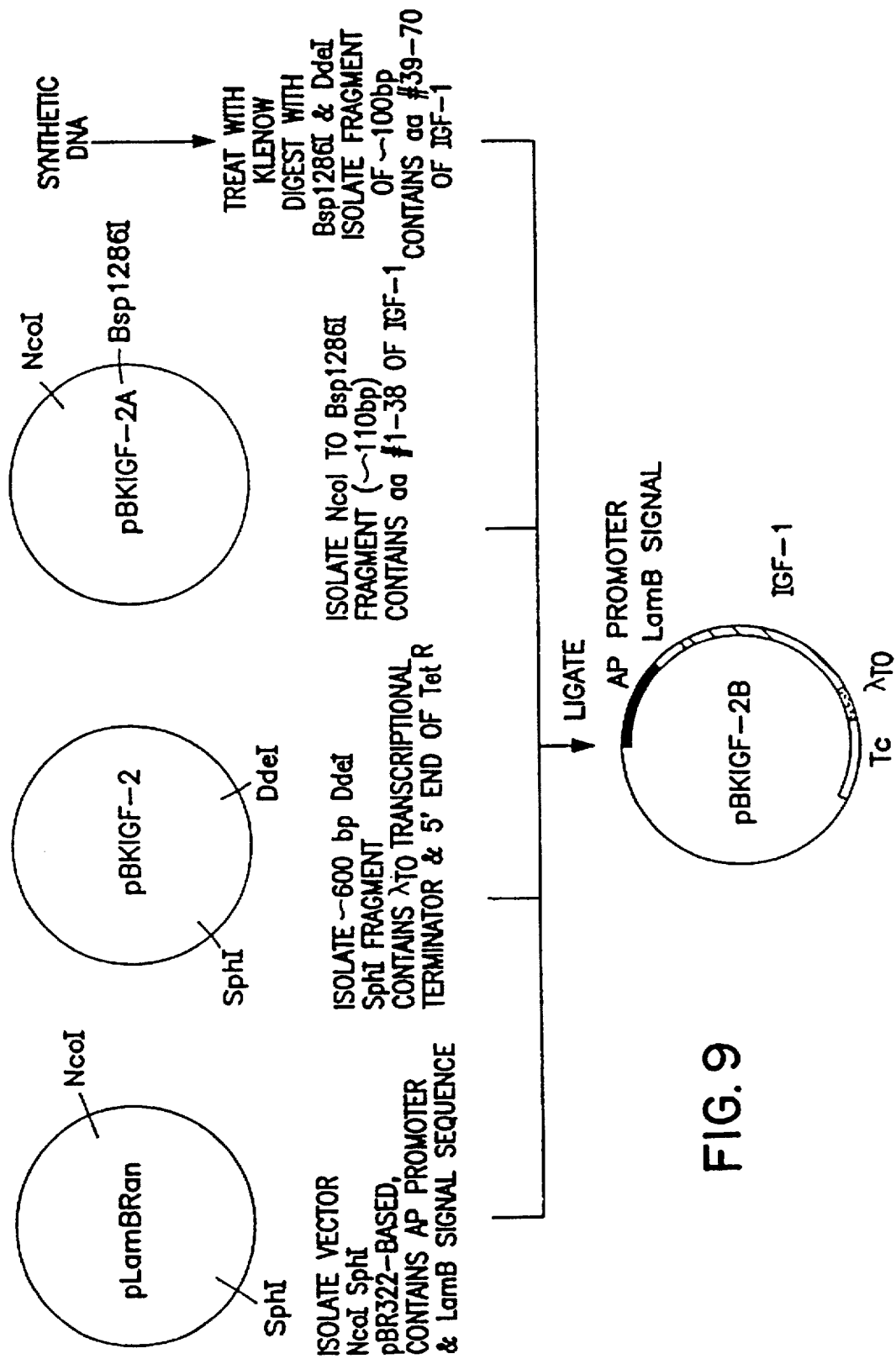
FIG. 9 depicts the construction of expression vector pBKIGF-2B from pBKIGF-2, pBKIGF-2A, pLamBRan, and a piece of synthetic DNA (SEQ. ID NOS. 8 and 9).

The construction of this plasmid is shown in FIG. 9. pLamBRan was digested with NcoI and SphI and the vector fragment was isolated containing the promoter and signal sequence. pBKIGF-2 was digested with DdeI and SphI and the ~600-bp fragment was isolated containing the lambda transcriptional terminator and the 5' end of the Tet$^R$ gene. pBKIGF-2A was digested with NcoI and Bsp1286I and the ~110-bp fragment was isolated containing the DNA encoding amino acids 1–38 of IGF-I. These three fragments were ligated together with synthetic DNA encoding amino acids 39–70 of IGF-I to yield pBKIGF-2B. This synthetic linker has the sequence:

```
5'-TCGTCGTGCTCCC CAG ACT GGT ATT GTT GAC GAA TGC TGC TTT CGT TCT TGC GAC CTG CGT CGT CTG -3'
(SEQ. ID NO. 8)
                                    3'- AGA ACG CTG GAC GCA GCA GAC CTT
TAC ATA ACG CGA GGG GAC TTT GGG CGATTTAGACGAATCTTCGAGG-5'
(SEQ. ID NO. 9)
```

C. Fermentation and Recovery Procedure i. Transformation

Competent *E. coli* 27C7 cells were transformed with pBKIGF-2B by standard transformation techniques. Transformants were selected and purified on LB plates containing 20 mg/L tetracycline. This medium had the following composition: 10 g/L Bacto-Tryptone, 5 g/L yeast extract, 10 g/L sodium chloride, and 20 mg/L tetracycline-HCl.

ii. Fermentation Inoculum

A 10-L fermentor inoculum was prepared by first inoculating a two-liter shake flask containing approximately 500 mL of sterile LB medium containing tetracycline with the freshly thawed 1–2 mL culture vial described above. This flask was incubated at 35°–39° C. for 8 hours and transferred into a 10-liter fermentor containing the production medium in the range of that described in Section C of this Example. The 10-liter fermentor inoculum was incubated at 35°–39° C. at pH 7.1–7.5 for 6–12 hours. The agitation rate was set at 650–1000 rpm and the aeration rate at 0.7–1.5 volumes of air per volume of culture per minute. The inoculum was then aseptically transferred to a 1000-L fermentation vessel wherein glucose is introduced from the bottom.

The 10-L inoculum was grown like the 500-mL shake flask cultivation to mid-exponential phase (batch cultivation). All the glucose was added to the 10-L fermentor at the start of the fermentation. Only the 1000-L fermentation utilized glucose feeding.

iii. Fermentation Procedure

The 1000-L vessel initially contained 600–800 liters of fermentation medium composed as follows:

| Ingredient | Quantity/Liter |
|---|---|
| glucose* | 250–350 g |
| ammonium sulfate | 3–8 g |
| ammonium hydroxide | as required to control pH 7.1 to 7.5 |
| sodium phosphate, monobasic dihydrate | 1–2 g |
| potassium phosphate, dibasic | 2–4 g |
| sodium citrate, dihydrate | 0.5–1.5 g |
| potassium chloride | 1–2.5 g |
| 25% Pluronic Polyol L61 | 0.1–0.2 mL initially and as needed to control foaming |
| magnesium sulfate, heptahydrate | 1–3 g |
| tetracycline HCl | 5–20 mg |
| yeast extract** | 5–20 g |
| NZ amine AS** | 5–25 g |
| isoleucine | 0–10 g |
| methionine** | 0–1 g |
| ferric chloride, heptahydrate | 10–30 mg |
| zinc sulfate, heptahydrate | 2–5 mg |
| cobalt chloride, hexahydrate | 2–5 mg |
| sodium molybdate, dihydrate | 2–5 mg |
| cupric sulfate, pentahydrate | 2–5 mg |
| boric acid | 0.5–2 mg |
| manganese sulfate, monohydrate | 1–3 mg |

| Ingredient | Quantity/Liter |
|---|---|

*1–5 g/L of glucose was added to the culture initially. The remainder was fed to the culture over the course of the fermentation.

**Yeast extract, NZ amine AS, and methionine can be added initially and/or fed throughout the fermentation.

The fermentation process was performed at 35°–39° C. at pH 7.1–7.5 for 24–48 hours. The agitation rate was set at 200 rpm and the aeration rate at 0.7–1.5 volumes of air per volume of culture per minute. Production of IGF-I occurred after the phosphate in the medium was depleted. This procedure resulted in fermentation broth containing approximately 18% packed cell volume and over 3 g/L IGF-I, which was principally in the periplasmic space with low levels in the extracellular medium.

D. In-situ Solubilization

At the end of fermentation, all feeds and controllers, with the exception of temperature, were turned off. Temperature control was maintained at 37° C. The sparge was shut off and fermentor back pressure was released. The broth volume was drained to 1200 L and the agitation was lowered from 200 rpm to 150 rpm. The sparge lines and fermentor headspace were then flushed with nitrogen gas, first at a rate of 150 Lpm for 1 minute, then at 50 Lpm for the remainder of the procedure. A 220-L slurry containing 174 kg of urea was then pumped rapidly into the fermentor, followed immediately by approximately 8 L of 50% (w/w) sodium hydroxide, sufficient to adjust the pH to 10.0. A 20-L solution containing 2.9 kg of dithiothreitol was then added and the pH was re-adjusted to 10.0 with approximately 3 additional liters of 50% sodium hydroxide. The batch was held with agitation at 37° C. for 60 minutes, after which it was cooled to 22° C. and transferred to a hold tank for aqueous two-phase extraction. Assays by reversed-phase HPLC showed that the initial titer of IGF-I was 3.8 g/L, and after solubilization IGF-I was quantitatively released from the cells.

E. Aqueous Two-Phase Liquid-Liquid Extraction

The batch temperature was maintained at 22° C. and the tank headspace was flushed with nitrogen. To the treated broth, having a volume of 1450 L, was added 250 kg of PEG-8000 and 90 kg of sodium sulfate. The batch was stirred for approximately 40 minutes. Centrifugation and analysis of samples showed that the phase-volume ratio (Kv) stabilized at 2.6 and the IGF-I distribution coefficient (Kc) was 8.5. The batch was separated using a Westfalia SB-7 separator, yielding approximately 1300 L of light phase and 550 L of heavy phase. Assays by reversed-phase HPLC showed that the isolated light phase contained approximately 88% of the IGF-I in the initial 1450 L of treated broth. The light phase was held under nitrogen and the heavy phase was discarded.

F. Precipitation of IGF-I

Approximately 36 L of 2M phosphoric acid was added to the light phase to adjust the pH to 7.0 at 22° C. The batch was held for approximately 8 hours with gently mixing, at which point assay by reversed-phase HPLC showed that approximately 96% of the IGF-I had precipitated. The pellet was then collected using a Westfalia SB-7 clarifier. The mass of the pellet slurry was approximately 88 kg.

G. Refolding

Figure 10:
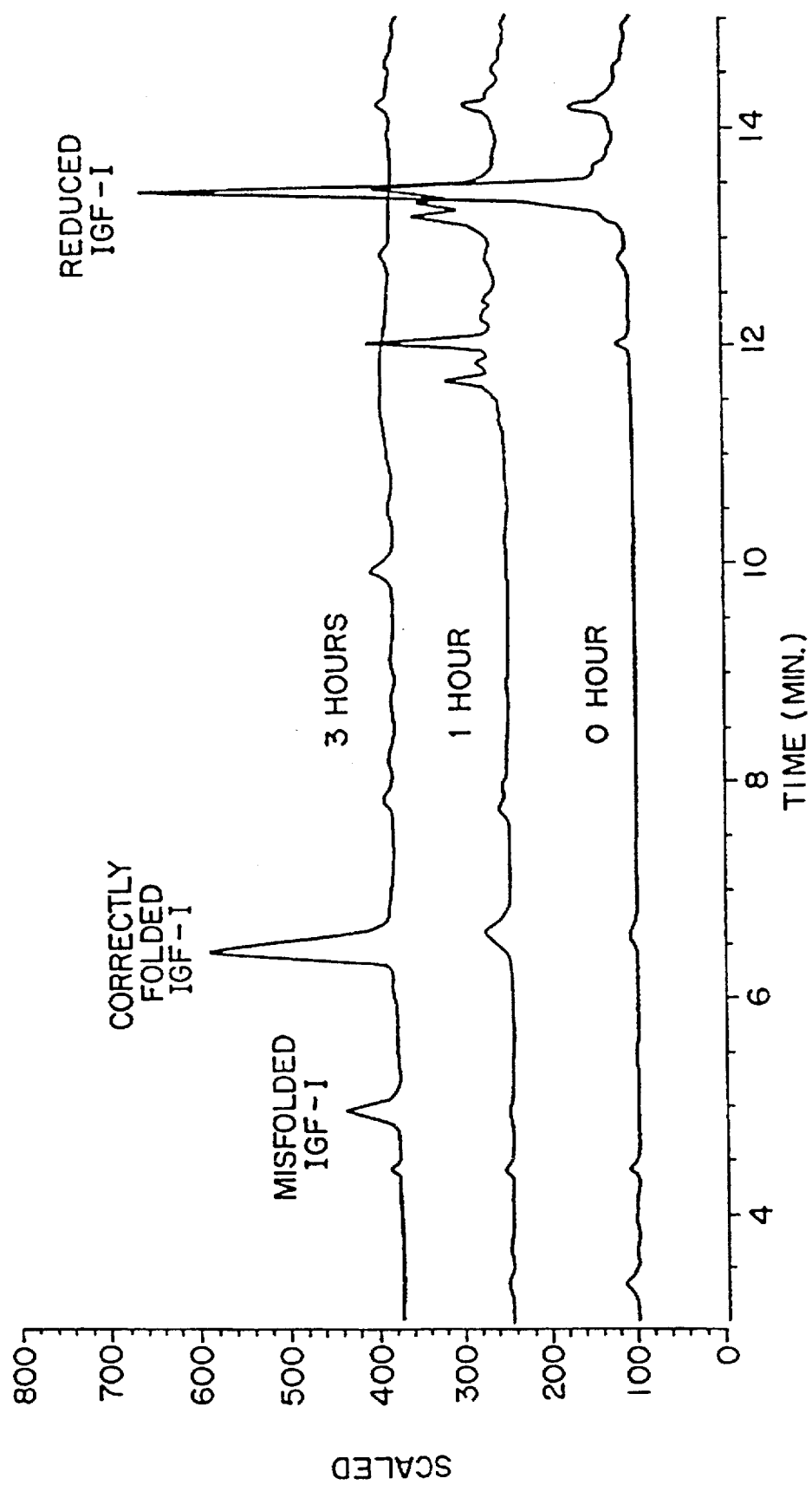
FIG. 10 is a series of three HPLC chromatograms showing the evolution of IGF-I species (from left to right, misfolded IGF-I, correctly folded IGF-I, and reduced IGF-I) during refolding. These chromatograms were taken at initiation of folding (bottom chromatogram), 1 hour after folding began (middle chromatogram), and 3 hours after folding began (top chromatogram).

An aliquot of the pellet slurry, having a mass of 17.6 kg, was dissolved by adding sufficient solid urea to bring the final concentration to 2M, by adding sufficient dithiothreitol to bring the concentration to 10 mM, and by adjusting the pH to 10.0 with 50% (w/w) sodium hydroxide. It was then added to 700 L of folding buffer having a composition of 2M urea, 1M sodium chloride, 19% (v/v) ethanol, 20 mM glycine, 0.5 µM copper, pH 10.5. The final concentration of dithiothreitol was then adjusted to 1 mM. Folding was carried out at 22° C. with gentle mixing by sparging in oxygen gas at 280 mL/minute. The progress of folding was monitored by reversed-phase HPLC. Representative HPLC chromatograms taken at the initiation of, at the middle of, and after termination of folding are shown in FIG. 10. After approximately 3 hours, folding was terminated by cessation of oxygen sparging and by titrating the batch to pH 3.5 with approximately 1.6 L of reagent phosphoric acid. Assay by reversed-phase HPLC showed that the yield of folding was 50%.

EXAMPLE II

The host construction, plasmid construction, and fermentation were carried out as described in Example I, parts A–C. In-situ solubilization was carried out as described in Example I, part D, except that instead of using DTT, the broth was reduced by the addition of sufficient L-cysteine to bring the final concentration to 50 mM (approximately 8.8 kg). At the end of solubilization, assay by reversed-phase HPLC showed that 93% of the IGF-I was released from the cells.

Subsequent isolation was carried out by scaled-down versions of the operations described in Example I, Parts E–G.

EXAMPLE III

Non-native IGF-I was prepared using the host, plasmid, fermentation, and in-situ solubilization procedure described in Example I, parts A–D.

Aqueous two-phase systems were produced using the following procedure: (1) phase-forming species were placed in a graduated 15-ml polystyrene culture tube; (2) 7 mL of whole extract from in-situ solubilization was added, the contents were mixed, and the headspace was flushed with nitrogen; (3) the composition was incubated for two hours at either room temperature or 37° C. with end-over-end mixing. Polymers were added from stock solutions (50% w/w PEG Mr 3350 polymer, 50% w/w PEG Mr 8000 polymer, and 100% w/w DOW Polyglycol 15-200™ brand polymer), while salts were added as dry chemicals. Components were added to achieve a predetermined composition on a weight-to-weight basis, assuming that whole extract has a density of 1 g/mL.

Phases were separated by centrifugation at either 25° C. or 37° C. at about 1300 g for 20 minutes. The concentration of IGF-I in the top phase was determined by reversed-phase HPLC analysis. The concentration of IGF-I in the bottom phase was calculated using a mass balance assumption.

Three experiments were conducted in which the concentration and type of phase-forming polymer, concentration and type of phase-forming salt, concentration and type of non-phase-forming salt, and temperature were varied. Resulting systems could be visually characterized as belonging in one of the five categories listed: (1) one-phase systems, (2) two-phase systems in which solids sediment in the bottom phase, (3) two-phase systems in which some solids float in the bottom phase, (4) two-phase systems in which solids are distributed throughout both the top and bottom phases, and (5) two-phase systems in which solids are distributed in the top phase.

Figure 11:
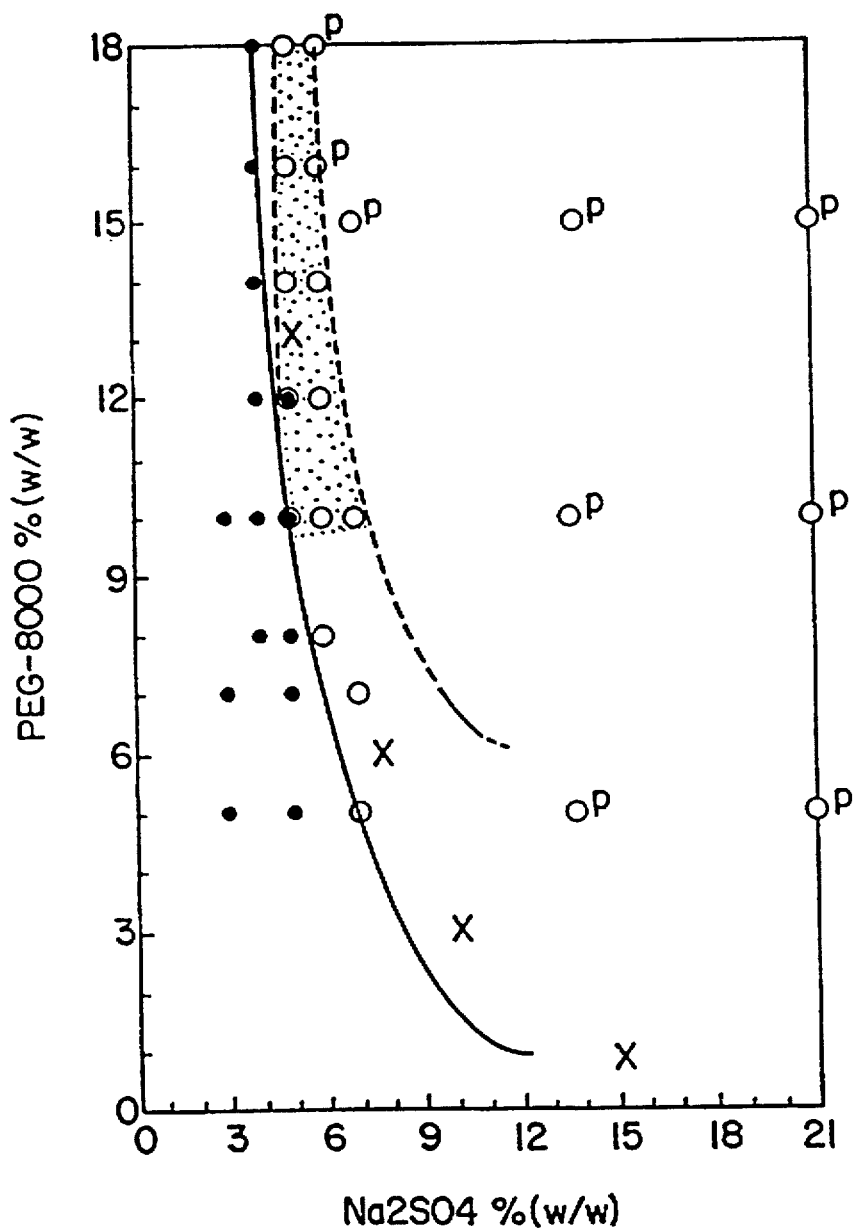
FIG. 11 is a phase diagram describing aqueous two-phase systems produced by adding salt and polymer to whole extract containing urea, DTT, non-native IGF-I, and cell-associated solids. Symbols are used to indicate two-phase systems (open circles), one-phase systems (filled circles), two-phase systems with floating solids (ρ), and published binodal points (X). Curves are used to show the approximate position of the binodal (solid), the limit for solid sedimentation (dashed), and the phase ratio limit allowing lower phase containment of solids (dotted). The shaded region indicates the optimum region for separation of IGF-I and cell-associated solids.

The plot shown in FIG. 11 illustrates this relationship between system composition and disposition for systems composed only of whole extract, PEG-8000, and $Na_2SO_4$. In this plot, "two-phase systems with floating solids" indicates all two-phase systems in which solids do not sediment in the bottom phase. The plot also indicates the limit describing systems in which solids are sedimented in a lower phase that is just large enough to accommodate their volume. The most preferable systems in which solids sediment in the bottom phase, the lower-phase volume is sufficient to accommodate solids, and the phase-volume ratio is greater than about 1 are contained within the shaded region.

These three experiments also provided data that allow the different aqueous two-phase systems to be quantitatively compared as shown in Table I. To reduce error and allow the effect of a given change to be more apparent, volume ratio and partition coefficient data were averaged for several different systems as indicated. Results from this analysis indicate several trends. The polymers PEG-8K and PEG-4K (having Mr values of 8000 and 3350, respectively) form systems having similar volume ratios in which non-native IGF-I partitions similarly. Including NaCl in examined phase systems does not affect the volume ratio but does decrease the IGF-I partition coefficient. Adding the random polyethylene glycol, polypropylene glycol copolymer DOW Polyglycol 15–200™ brand polymer (Mr ~2500) does not alter the volume ratio or partition coefficient. Including the phase-forming salt citrate in PEG-8000 and $Na_2SO_4$ systems shifts the position of the binodal curve but does not affect IGF-I partitioning. Conducting aqueous two-phase extraction at 37° C. decreases the volume ratio and partition coefficient relative to 25° C.

TABLE I

Averaged Effect of Aqueous Two-Phase Effectors on Kv and Kc

| Condition | n | Kv | Kc | Averaged Over |
|---|---|---|---|---|
| Experiment #1 | | | | |
| 7% $Na_2SO_4$/PEG-8K | 6 | 1.09 | 2.5 | [PEG] = 10, 15% (w/w) |
| | | | | [NaCl] = 0, 3, 6% (w/w) |
| 7% $Na_2SO_4$/PEG-4K Experiment #1 | 6 | 0.99 | 2.7 | |
| 7% $Na_2SO_4$ | 4 | 1.03 | 2.9 | [PEG] = 10, 15% (w/w) |
| | | | | PEG Mr = 4, 8 kD |
| 7% $Na_2SO_4$, 6% NaCl Experiment #2 | 4 | 1.06 | 2.3 | |
| 7% $Na_2SO_4$/PEG-8K | 9 | 0.58 | 1.6 | [PEG-8K] = 5, 7, 10% (w/w) |
| | | | | [NaCl] = 0, 3% (w/w) |
| | | | | [Citrate] = 0, 3% (w/w) |
| 7% $Na_2SO_4$/PEG-8K + 2% EP15-200 **Experiment #2 | 9 | 0.57 | 1.5 | |
| 7% $Na_2SO_4$ | 6 | 0.60 | 1.6 | [PEG-8K] = 5, 7, 10% (w/w) |
| | | | | [EP15-200] = 0, 2% (w/w) |
| 5% $Na_2SO_4$, 3% citrate Experiment #3 | 6 | 0.60 | 1.5 | |
| 25° C. | 6 | 1.95 | 2.0 | [PEG-8K] = 12, 14, 16% (w/w) |
| | | | | [$Na_2SO_4$] = 5, 6% (w/w) |
| 37° C. | 6 | 1.76 | 1.8 | |

**Data were averaged in a manner to account for changes in the position of the binodal curve.

EXAMPLE IV

Non-native IGF-I was prepared using the host, plasmid, fermentation, and in-situ solubilization procedure described in Example I, parts A–D.

Aqueous two-phase systems were produced as described in Example III with the exception that PEG-8000 was added in dry form rather than as a stock solution. The concentrations of IGF-I in the top phase and bottom liquid phase were determined by reversed-phase HPLC analysis. The bottom liquid phase was subjected to 0.2 μm filtration prior to analysis to remove residual suspended solids.

Results of direct determination of the partition coefficient of non-native IGF-I in aqueous two-phase systems are shown in Table II. With a condition of 5% (w/w) $Na_2SO_4$, 14% (w/w) PEG-8000, the distribution coefficient has a magnitude of 9 to 10. A 1% (w/w) increase in the salt concentration or a 2% (w/w) increase in the polymer concentration doubles its magnitude. Combined increases in the salt and polymer concentrations lead to a four-fold increase, resulting in a value near 40. This latter combination results in formation of a two-phase system with floating solids.

TABLE II

Partition Coefficient of Whole-Extract IGF-I in PEG-8000, $Na_2SO_4$ Aqueous Two-Phase Systems

| $Na_2SO_4$ | PEG-8K (% w/w) | | |
|---|---|---|---|
| (% w/w) | 12 | 14 | 16 |
| 5 | | 9.0 | 19.1 |
| | 1-phase | 2.38 | 2.04 |
| | | 96 | 98 |
| 6 | 12.0 | 21.9 | 41 |
| | 1.29 | 1.31 | 1.24 |
| | 94 | 97 | 98 |

Values indicate, from top to bottom, respectively: IGF-I distribution coefficient (measured), phase-volume ratio, and mass percentage of soluble whole-extract IGF-I in top phase.

EXAMPLE V

Non-native IGF-I was prepared using the fermentation, in situ solubilization, and aqueous two-phase extraction procedures as described in Example I, Parts A–E. For IGF-I precipitation, a portion of the light phase was divided into several aliquots that were then titrated to approximately pH 6 using one of the following acids: 2N phosphoric, 2N acetic, 2N sulfuric, 2N hydrochloric, 2N citric, or 2N nitric acid. The aliquots were then centrifuged briefly at approximately 5000 x g for 15 minutes and the supernatant liquids were decanted. Assays by reversed-phase HPLC showed that, in all cases, at least 93% of the starting IGF-I was recovered in the pellet. Subsequent protein folding of pellets was carried out by a scaled-down version of the procedure described in Example I, Part G.

EXAMPLE VI

Non-native IGF-I was prepared using the fermentation, in situ solubilization, and aqueous two-phase extraction procedures as described in Example I, Parts A–E.

A sample of the light phase from part E of Example I was divided into several smaller aliquots, and acid precipitation was initiated by titrating these aliquots to either pH 10, 4.5, 4.0, 3.5, or 3.0 using 2M sulfuric acid. Each of these five stocks was then further divided into five aliquots, which received solid sodium sulfate sufficient to give a final concentration of either 3, 4, 5, 6, or 7% by weight. The samples were incubated for two hours at 25° C. with gentle mixing. The phases were then separated after centrifugation at approximately 5000 x g for 20 minutes. The concentration of IGF-I in both phases was assayed by reversed-phase HPLC.

For all sodium sulfate levels at pH 10, greater than 95% of the IGF-I remained in the top phase. For all samples at all other pHs (4.5 to 3.0), greater than 98% of the IGF-I was recovered in the bottom phase.

EXAMPLE VII

Non-native IGF-I was prepared using the fermentation, in-situ solubilization, aqueous two-phase extraction, and neutralization precipitation procedure described in Example 1, Parts A–G.

A suspension containing reduced IGF-I was prepared from IGF-I pellet obtained by neutralization precipitation. To produce this suspension 30 g of wet pellet containing IGF-I was resuspended in a solution containing 20 mM glycine (pH 10.5), 2M urea, and 10 mM DTT to a final volume of 100 mL. The pH of the resulting suspension was adjusted to pH 10.5 by addition of NaOH and HCl as required. Reversed-phase HPLC analysis of the suspension indicated that it contained 35 mg/mL IGF-I.

Refolding buffers were prepared in 15-mL polystyrene culture tubes by addition of appropriate amounts of the following stock solutions: 1M glycine (pH 10.5) and 25 µM $CuCl_2$, 9M urea, 100% ethanol, 1.8M $Na_2SO_4$, 20% (v/v) PEG-3350, and 20% (v/v) PEG-8000. Each tube received 0.1 mL of the 50 X buffer stock solution containing glycine and $CuCl_2$. Other stocks were added so as to have the indicated concentration at a final volume of 5 mL. Each tube containing refolding buffer components was brought to a final volume of 4 mL.

IGF-I refolding was initiated by diluting 1 mL of reduced IGF-I suspension into the previously prepared refolding buffers, giving an initial IGF-I concentration of 7 mg/mL. Tubes were capped and shaken horizontally on an orbital shaker. Each tube contained 5 mL of liquid and 10 mL of air. Refolding was allowed to occur for three hours after which samples were collected, diluted by a factor of 10 into an acidified buffer containing 20 mM glycine (pH 3), 2M urea, and analyzed by reversed-phase HPLC to determine the content of correctly folded IGF-I.

The object of this example is to show the effect of aqueous phase-forming components on yield of correctly folded IGF-I obtained during refolding. The specific phase-forming components investigated were $Na_2SO_4$, PEG-3350, PEG-8000, and ethanol. The concentrations examined were consistent with those which may be produced by diluting an isolated aqueous phase by a factor of 10 to 15.

Results, shown in Table III, indicate that yield of correctly folded IGF-I is enhanced by refolding IGF-I in the presence of the phase-forming components ethanol and $Na_2SO_4$. Yield of IGF-I is not affected by the presence of the phase-forming components PEG-3350 or PEG-8000.

TABLE III

Effect of Aqueous Phase-Forming Species on IGF-I Refolding Yield

| $Na_2SO_4$ (M) | No PEG | PEG-3350 0.88% (w/w) | PEG-8000 1.05% (w/w) |
|---|---|---|---|
| | | No Ethanol | |
| 0 | 11.4% | 11.6% | 11.3% |
| 0.1 | 11.9% | 11.6% | 11.4% |
| 0.3 | 9.4% | 9.7% | 9.3% |
| 0.6 | 4.4% | 4.0% | 3.8% |
| | | 20% (v/v) Ethanol | |
| 0 | 22.7% | 23.04% | 23.6% |
| 0.1 | 25.7% | * | 23.2% |
| 0.3 | 28.4% | 28.3% | 28.3% |
| 0.6 | 26.4% | 25.8% | 25.8% |

The initial concentration of IGF-I was 7 mg/mL.

EXAMPLE VIII

Non-native IGF-I was prepared using the fermentation, in-situ solubilization, aqueous two-phase extraction, and neutralization precipitation procedures described in Example I, Parts A–G.

A suspension containing reduced IGF-I was prepared from IGF-I pellet obtained by neutralization precipitation. To produce this suspension, 10 g of wet pellet containing IGF-I was resuspended in 45 mL of a solution containing 20 mM glycine (pH 10.5), 2M urea, and 10 mM DTT. The pH of the resulting suspension was adjusted to pH 10.5 by addition of NaOH as required. Reversed-phase HPLC analysis of the pH-adjusted suspension indicated that it contained 15 mg/mL IGF-I. The pH-adjusted suspension was spiked with a concentrated DTT solution to obtain a final DTT concentration of 15 mM. The resulting reduced IGF-I suspension contained 15 mg/mL IGF-I, 20 mM glycine (pH 10.5), 2M urea, and 15 mM DTT.

Refolding buffers were prepared in 15-mL polystyrene culture tubes by addition of appropriate amounts of various stock solutions and dry chemicals. Each tube received 0.1 mL of a 50 X buffer stock solution containing 1M glycine (pH 10.5), and 25 µM $CuCl_2$. Appropriate amounts of other chemicals were added so as to have the indicated concentration at a final volume of 5 mL. Ethanol and glycerol were added as liquids. Urea, NaCl, and $Na_2SO_4$ were added in dry form. Each tube containing refolding buffer components was brought to a final volume of 4.7 or 3.7 mL depending on whether refolding was to be conducted at 1 or 4 mg/mL IGF-I, respectively.

IGF-I refolding was initiated by diluting 0.3 or 1.3 mL of reduced IGF-I suspension, for refolding at 1 or 4 mg/mL IGF-I, respectively, into the previously prepared refolding buffers. Tubes were capped and shaken horizontally on an orbital shaker. Each tube contained 5 mL of liquid and 10 mL of air. Refolding was allowed to occur for 8 hours after which samples were collected, acidified, and analyzed by reversed-phase HPLC to determine the content of correctly folded IGF-I.

The following aspects of refolding buffer composition were investigated: salt type and concentration (0, 0.5, 1.0M NaCl; or 0, 0.2, 0.6M $Na_2SO_4$), chaotrope concentration (1, 2, 3M urea), solvent concentration (0, 10, 20% v/v ethanol), osmolyte concentration (0, 20, 30% v/v glycerol), and initial IGF-I concentration (1, 4 mg/mL). The yields obtained with select combinations of these components are shown in Table IV. Inspection shows that the highest yield of correctly folded IGF-I was obtained by refolding at the following condition: 1 mg/mL IGF-I, 20 mM glycine (pH 10.5), 2M urea, 1M NaCl, 20% (v/v) ethanol, and 0.5 µM $CuCl_2$ (sample #0).

The experiment described in this example was designed to allow multifactorial statistical analysis of correctly folded IGF-I yield data in order to assess the importance of all single factors and all two-factor interactions. The results from this statistical analysis are shown in Tables V and VI. Inspection of these results shows that, under the experimental conditions employed, the following trends were apparent: (1) best yields are obtained by refolding at low IGF-I concentration; (2) including salt at a concentration of about 1M improves refolding yield particularly in the presence of ethanol; (3) NaCl is a more preferred salt than is $Na_2SO_4$; (4) better yield is obtained with refolding in 2–3M urea relative to lower urea concentration, although the difference is diminished in the presence of ethanol; (5) improved yield is obtained in the presence of 20% (v/v) ethanol relative to absence of solvent; and (6) including glycerol improves yield but its advantage is reduced in the presence of ethanol.

TABLE IV

Effect of Solution Conditions on IGF-I Refolding Yield

| Sample # | Salt | [Salt] (M) | [IGF-I] (mg/mL) | [urea] (M) | [ethanol] % (v/v) | [glycerol] (v/v) | Yield IGFI (%) |
|---|---|---|---|---|---|---|---|
| 0 | NaCl | 1 | 1 | 2 | 20 | 0 | 50 |
| 1 | NaCl | 1 | 1 | 3 | 20 | 30 | 39 |
| 2 | NaCl | 1 | 1 | 3 | 0 | 0 | 33 |
| 3 | NaCl | 0 | 1 | 3 | 20 | 0 | 38 |
| 4 | NaCl | 0 | 1 | 3 | 0 | 30 | 34 |
| 5 | NaCl | 1 | 1 | 1 | 20 | 0 | 49 |
| 6 | NaCl | 1 | 1 | 1 | 0 | 30 | 36 |
| 7 | NaCl | 0 | 1 | 1 | 20 | 30 | 34 |
| 8 | NaCl | 0 | 1 | 1 | 0 | 0 | 23 |
| 9 | NaCl | 0.5 | 1 | 2 | 10 | 20 | 44 |
| 10 | NaCl | 0.5 | 1 | 2 | 10 | 20 | 45 |
| 11 | NaCl | 1 | 4 | 3 | 20 | 0 | 33 |
| 12 | NaCl | 1 | 4 | 3 | 0 | 30 | 27 |
| 13 | NaCl | 0 | 4 | 3 | 20 | 30 | 24 |
| 14 | NaCl | 0 | 4 | 3 | 0 | 0 | 15 |
| 15 | NaCl | 1 | 4 | 1 | 20 | 30 | 31 |
| 16 | NaCl | 1 | 4 | 1 | 0 | 0 | 7 |
| 17 | NaCl | 0 | 4 | 1 | 20 | 0 | 21 |
| 18 | NaCl | 0 | 4 | 1 | 0 | 30 | 19 |
| 19 | NaCl | 0.5 | 4 | 2 | 10 | 20 | 30 |
| 20 | NaCl | 0.5 | 4 | 2 | 10 | 20 | 31 |
| 21 | Na$_2$SO$_4$ | 0.6 | 1 | 3 | 20 | 0 | 32 |
| 22 | Na$_2$SO$_4$ | 0.6 | 1 | 3 | 0 | 30 | 36 |
| 23 | Na$_2$SO$_4$ | 0 | 1 | 3 | 20 | 30 | 31 |
| 24 | Na$_2$SO$_4$ | 0 | 1 | 3 | 0 | 0 | 28 |
| 25 | Na$_2$SO$_4$ | 0.6 | 1 | 1 | 20 | 30 | 37 |
| 26 | Na$_2$SO$_4$ | 0.6 | 1 | 1 | 0 | 0 | 11 |
| 27 | Na$_2$SO$_4$ | 0 | 1 | 1 | 20 | 0 | 36 |
| 28 | Na$_2$SO$_4$ | 0 | 1 | 1 | 0 | 30 | 29 |
| 29 | Na$_2$SO$_4$ | 0.2 | 1 | 2 | 10 | 20 | 45 |
| 30 | Na$_2$SO$_4$ | 0.2 | 1 | 2 | 10 | 20 | 45 |
| 31 | Na$_2$SO$_4$ | 0.6 | 4 | 3 | 20 | 30 | 29 |
| 32 | Na$_2$SO$_4$ | 0.6 | 4 | 3 | 0 | 0 | 9 |
| 33 | Na$_2$SO$_4$ | 0 | 4 | 3 | 20 | 0 | 26 |
| 34 | Na$_2$SO$_4$ | 0 | 4 | 3 | 0 | 30 | 24 |
| 35 | Na$_2$SO$_4$ | 0.6 | 4 | 1 | 20 | 0 | 29 |
| 36 | Na$_2$SO$_4$ | 0.6 | 4 | 1 | 0 | 30 | 12 |
| 37 | Na$_2$SO$_4$ | 0 | 4 | 1 | 20 | 30 | 24 |
| 38 | Na$_2$SO$_4$ | 0 | 4 | 1 | 0 | 0 | 9 |

TABLE V

Average Yield of Correctly Folded IGF-I by Refolding Solution Component

A. By Initial IGF-I Concentration

| [IGF-I] (mg/mL) | Yield IGF-I (%) |
|---|---|
| 1.0 | 32.9 |
| 4.0 | 21.2 |

B. By Salt Type

| Salt | Yield IGF-I (%) |
|---|---|
| NaCl | 29.1 |
| Na$_2$SO$_4$ | 25.1 |

C. By Salt Level

| Salt Level | Yield IGF-I (%) |
|---|---|
| None | 26.0 |
| High | 28.2 |

D. By Urea Concentration

| [Urea] | Yield IGF-I (%) |
|---|---|
| 1.0 | 25.4 |
| 3.0 | 28.8 |

E. By Ethanol Concentration

| [Ethanol] (% v/v) | Yield IGF-I (%) |
|---|---|
| 0.0 | 22.1 |
| 20.0 | 32.0 |

F. By Glycerol Concentration

| [Glycerol] (% v/v) | Yield IGF-I (%) |
|---|---|
| 0.0 | 24.9 |
| 30.0 | 29.3 |

TABLE VI

Average Yield of Correctly Folded IGF-I by Refolding Solution Component Combinations A. By Ethanol and Glycerol Concentration

| | No Glycerol | 30% Glycerol |
|---|---|---|
| No Ethanol | 16.9 | 27.3 |
| 20% Ethanol | 32.9 | 31.2 |

B. By Ethanol and Urea Concentration

| | 1 M Urea | 3 M Urea |
|---|---|---|
| No Ethanol | 18.3 | 25.9 |
| 20% Ethanol | 32.5 | 31.6 |

C. By Ethanol and Salt Concentration

| | No Salt | High Salt |
|---|---|---|
| No Ethanol | 22.9 | 21.4 |
| 20% Ethanol | 29.2 | 34.9 |

D. By Salt Type and Salt Level

| | No Salt | High Salt |
|---|---|---|
| NaCl | 26.1 | 32 |
| Na$_2$SO$_4$ | 25.9 | 24.3 |

EXAMPLE IX

A reduced IGF-I stock solution was prepared from highly purified, correctly folded IGF-I. A solution containing 1 mg/mL IGF-I, 20 mM glycine (pH 10.5), 2 mM citrate, 0.1M NaCl, and 2M urea was placed in a stoppered vial and the headspace was flushed with humidified argon gas for about one hour with occasional swirling. Following solution deoxygenation, DTT was added via syringe from a 117 mM stock solution to a final concentration of 1.17 mM. Following DTT addition, the solution was incubated for two hours with continued argon headspace flushing.

Refolding solutions were prepared from a common buffer stock solution containing 20 mM glycine (pH 10.5), 0.1M NaCl, and 2M urea. This buffer stock was dispensed in vials and CuCl$_2$, NiCl$_2$, ZnCl$_2$, CoCl$_2$, MnCl$_2$, and FeCl$_3$ were added separately from 1.3 mM stock solutions. Vials containing resulting solutions were stoppered, and the liquid was sparged continuously with either humidified argon or oxygen.

To initiate a refolding reaction, an aliquot of reduced IGF-I stock solution was rapidly diluted by a factor of 10 into a refolding solution. The reduced IGF-I stock solution was transferred via syringe to initiate refolding. Control refolding reactions (lacking transition metal salt) and test refolding reactions were conducted simultaneously and shared a common gas source.

Samples were collected by syringe from refolding reactions after 18 minutes of oxidation and rapidly added to septum-covered microvials containing a small amount of 6N HCl. The extent of IGF-I refolding was determined by analyzing samples by reversed-phase HPLC.

As shown in Table VII, exposing reduced IGF-I to oxygen in the presence of either CuCl$_2$ or MnCl$_2$ led to both oxidation of reduced IGF-I and formation of correctly folded IGF-I. The presence of CoCl$_2$ led to oxidation of reduced IGF-I but formation of less correctly folded IGF-I. Both NiCl$_2$ and FeCl$_3$ resulted in yet less oxidation of reduced IGF-I and formation of correctly folded IGF-I. The response to ZnCl$_2$ was not different from that to trace elements.

TABLE VII

Oxidation Catalysis with Various Transition Metal Ions

| Condition | % Correctly Folded IGF-I | % Reduced IGF-I Remaining |
|---|---|---|
| Argon, trace | 0 | 77 |
| O$_2$, trace | 0 | 59 |
| O$_2$, 13 µM CuCl$_2$ | 13 | 0 |
| O$_2$, 13 µM NiCl$_2$ | 1.5 | 37 |
| O$_2$, 13 µM ZnCl$_2$ | 0 | 61 |
| O$_2$, 13 µM CoCl$_2$ | 2.3 | 3.8 |
| O$_2$, 13 µM MnCl$_2$ | 11 | 3.3 |
| O$_2$, 13 µM FeCl$_3$ | 1.6 | 29 |

EXAMPLE X

A reduced IGF-I stock solution was prepared from highly purified, correctly folded IGF-I as described in Example IX.

Refolding solutions were prepared from a common buffer stock solution containing 20 mM glycine (pH 10.5), 0.1M NaCl, and 2M urea. This buffer stock was dispensed in vials and CuCl$_2$ was added separately as required from 1.3, 0.13, 0.013, and 0.0013 mM stock solutions that had been previously prepared by serial dilution. After CuCl$_2$ was added, vials were stoppered and the liquid was sparged continuously with either humidified argon or oxygen.

To initiate a refolding reaction, an aliquot of reduced IGF-I stock solution was rapidly diluted by a factor of ten into a refolding solution. The reduced IGF-I stock solution was transferred via syringe to initiate refolding. Control refolding reactions (lacking CuCl$_2$) and test refolding reactions were conducted simultaneously and shared a common gas source.

Samples were collected by syringe from refolding reactions at predetermined intervals and rapidly added to septum-covered microvials containing a small amount of 6N HCl. This treatment lowers the pH of the sample to pH 3 and effectively quenches the refolding reaction. Samples were collected and quenched at the following times post-refolding initiation: 0, 2, 4, 6, 10, 20, 40, 60, 100, and 200 minutes. The extent of IGF-I refolding with time was determined by analyzing time-course samples by reversed-phase HPLC.

The following concentrations of CuCl$_2$ were investigated: trace, 0.013 µM, 0.052 µM, 0.13 µM, 0.52 µM, 1.3 µM, 5.2 µM, and 13 µM CuCl$_2$. A plot of the evolution of correctly folded IGF-I during aerobic oxidation catalysis at these CuCl$_2$ concentrations is shown in FIG. 12.

Results show that during aerobic oxidation catalysis, a low CuCl$_2$ concentration (between about 0.05 µM and 15 µM, preferably between 0.05 and 0.5 µM) provides higher yield of correctly folded polypeptide than higher concentrations (greater than about 15 µM) and provides more rapid and reproducible oxidation kinetics than trace-element catalysis.

Figure 12:
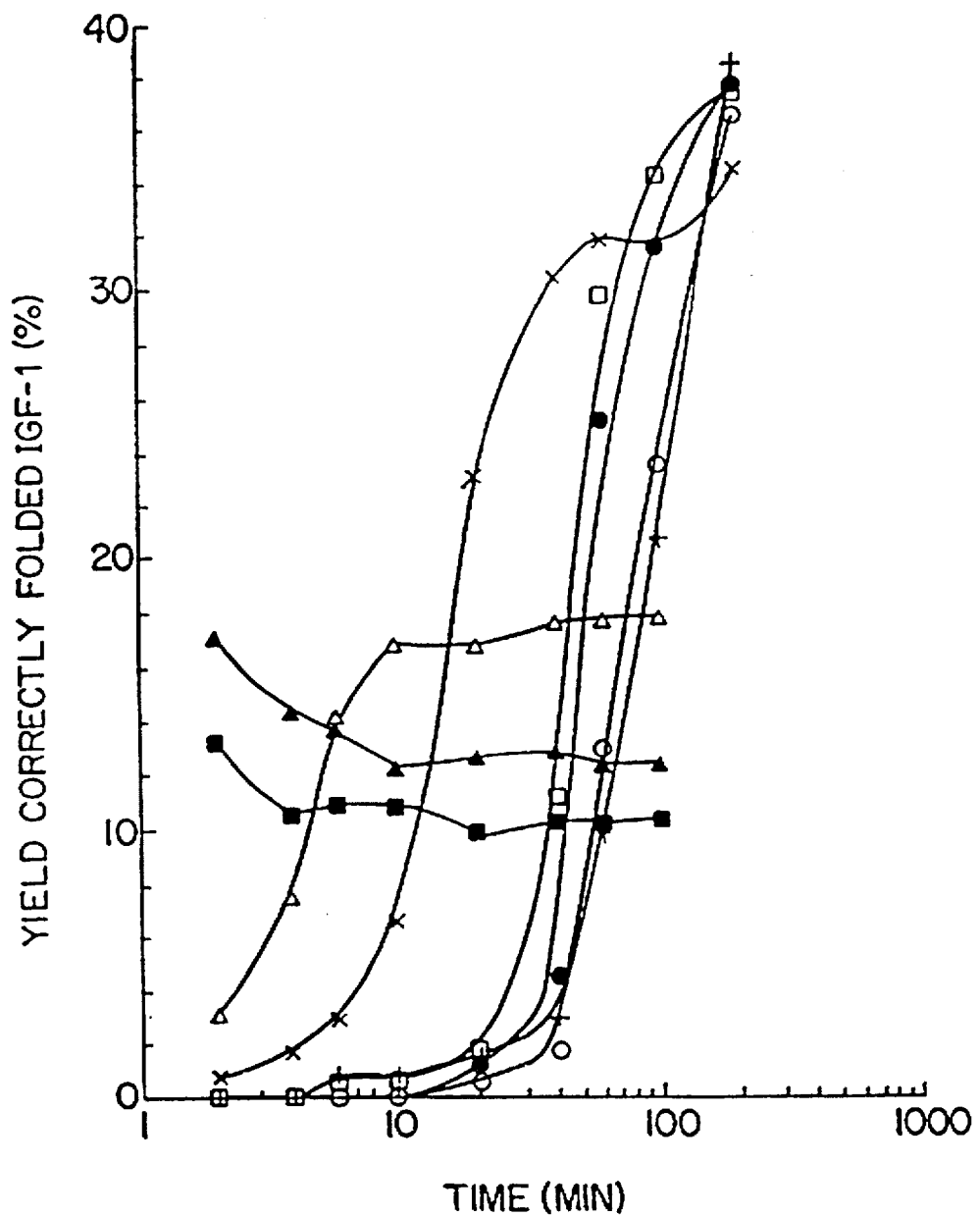
FIG. 12 shows the effect of copper concentration on the kinetics of IGF-I refolding. Refolding was conducted at 25° C. with copper chloride concentrations of trace (cross), 0.013 μM (open circle), 0.052 μM (filled circle), 0.13 μM (open square), 0.52 μM (asterisk), 1.3 μM (open triangle), 5.2 μM (filled triangle), and 13 μM (filled square).

The results shown in FIG. 12 were obtained by refolding IGF-I in solutions lacking alcoholic or polar aprotic solvent. Additional experiments showed that including alcohol in the refolding buffer did not influence the dependence of IGF-I refolding kinetics and yield on CuCl$_2$ concentration, and is not expected to influence the dependence on the concentration of other transition metals. Experiments also showed that including EDTA (1:1 molar ratio to CuCl$_2$) or o-phenanthroline (3:1 molar ratio to CuCl$_2$) in refolding solutions containing 1.3 µM CuCl$_2$ did not affect CuCl$_2$-catalyzed aerobic IGF-I oxidation kinetics.

What is claimed is:

1. A composition comprising about 0.1 to 15 mg/ml of an incorrectly folded polypeptide in a buffer of pH 7–12 comprising about 5–40% (v/v) of an alcoholic or polar aprotic solvent, about 0.2 to 3M of an alkaline earth, alkali metal, or ammonium salt, about 0.1 to 9M of a chaotropic agent, and about 0.01 to 15 µM of a copper or manganese salt.

2. The composition of claim 1 wherein the concentration of the solvent is about 10–30% (v/v).

3. The composition of claim 1 wherein the concentration of the polypeptide is about 0.1 to 6 mg/mL.

4. The composition of claim 1 wherein the concentration of the alkaline earth, alkali metal, or ammonium salt is about 0.2 to 2M.

5. The composition of claim 1 wherein the concentration of chaotropic agent is about 0.5 to 6M.

6. The composition of claim 1 wherein the concentration of copper or manganese salt is about 0.01 to 5 µM.

7. The composition of claim 1 wherein the concentration of copper or manganese salt is about 0.01 to 0.5 µM.

8. The composition of claim 1 wherein the solvent is methanol, ethanol, iso-propanol, n-propanol, t-butanol, dimethylsulfoxide, dimethylformamide, N-methylpyrrolidone, tetrahydrofuran, dioxane, glycerol, acetonitrile, or propylene glycol.

9. The composition of claim 1 wherein the chaotropic agent is urea.

10. The composition of claim 1 wherein the alkaline earth, alkali metal, or ammonium salt is 0.5 to 2M of a sodium, potassium, or ammonium salt or about 0.2 to 1M of a magnesium salt.

11. The composition of claim 10 wherein the solvent is ethanol and the alkaline earth, alkali metal, or ammonium salt is a chloride or sulfate salt, and the concentration of polypeptide ranges from about 0.2 to 5 mg/mL.

12. The composition of claim 11 wherein the polypeptide is IGF-I, growth hormone, or a neurotrophin, the alkaline earth, alkali metal, or ammonium salt is sodium chloride, and the pH of the buffer is from about 8 to 11.

13. The composition of claim 1 wherein the polypeptide is IGF-I.

14. The composition of claim 1 wherein the copper or manganese salt is a chloride or sulfate.

15. The composition of claim 14 wherein the copper salt is copper chloride.

16. The composition of claim 14 wherein the copper salt is present in a concentration of about 0.5 µM.

17. The composition of claim 1 wherein the buffer also comprises an osmolyte and a reducing agent.

18. The composition of claim 17 wherein the buffer is glycine, CAPS, or CAPSO.

19. The composition of claim 17 wherein the reducing agent is cysteine or dithiothreitol in a concentration of about 1–5 mM.

20. The composition of claim 19 wherein the buffer is glycine or CAPSO in a concentration of about 20 mM, the reducing agent is dithiothreitol in a concentration of about 1 mM, the copper salt is copper chloride, and the chaotropic agent is urea in a concentration of about 1 to 3M, wherein the buffer has a pH of about 8.5 to 11.

21. The composition of claim 20 wherein the urea is in a concentration of about 2M.

22. A process for increasing the yield of correct refolding of an incorrectly folded polypeptide contained in host cells, said process comprising the step of contacting said incorrectly folded polypeptide with a buffer, wherein during said process said incorrectly folded polypeptide is both unfolded and then refolded into its biologically active conformation while the polypeptide is present in a concentration of about 0.1 to 15 mg/mL of said buffer and said buffer has a pH of 7–12 and comprises about 5–40% (v/v) of an alcoholic or polar aprotic solvent, about 0.2 to 3M of an alkaline earth, alkali metal, or ammonium salt, about 0.1 to 9M of a chaotropic agent, and about 0.01 to 15 µM of a copper or manganese salt.

23. The process of claim 22 wherein the host cells are prokaryotic.

24. The process of claim 22 wherein the alkaline earth, alkali metal, or ammonium salt is about 0.5 to 2M of a sodium, potassium, or ammonium salt or about 0.2 to 1M of a magnesium salt.

25. The process of claim 22 wherein the buffer further comprises a reducing agent and an osmolyte.

26. The process of claim 22 wherein the copper salt is copper chloride.

27. A process for increasing the yield of correct refolding of a misfolded polypeptide contained in host cells, said process comprising the step of contacting said polypeptide with a buffer, wherein during the refolding step the polypeptide is present in a concentration of about 0.1 to 15 mg/mL of said buffer and wherein the buffer is CAPSO or glycine having a pH of about 8 to 11 and further comprises about 20% (v/v) of ethanol or isopropanol, about 0.2 to 3M sodium chloride, urea in a concentration of about 1–3M, a reducing agent which is dithiothreotol or cysteine, an osmolyte which is sucrose or glycerol and about 0.01 to 1 5 μM of copper chloride, wherein said polypeptide is IGF-1.

* * * * *